US009080181B2

(12) United States Patent
Arruda et al.

(10) Patent No.: US 9,080,181 B2
(45) Date of Patent: Jul. 14, 2015

(54) NUCLEIC ACID CONSTRUCTS METHODS FOR ALTERING PLANT FIBER LENGTH AND/OR PLANT HEIGHT

(75) Inventors: Paulo Arruda, Campinas (BR); Isabel Rodrigues Gerhardt, Campinas (BR)

(73) Assignee: FIBRIA CELULOSE S.A., Sao Paulo (BR)

( * ) Notice: Subject to any disclaimer, the term of this patent is extended or adjusted under 35 U.S.C. 154(b) by 1117 days.

(21) Appl. No.: 12/520,282

(22) PCT Filed: Dec. 20, 2007

(86) PCT No.: PCT/BR2007/000357
§ 371 (c)(1),
(2), (4) Date: Dec. 2, 2009

(87) PCT Pub. No.: WO2008/074115
PCT Pub. Date: Jun. 26, 2008

(65) Prior Publication Data
US 2010/0095405 A1    Apr. 15, 2010

Related U.S. Application Data

(60) Provisional application No. 60/871,048, filed on Dec. 20, 2006.

(51) Int. Cl.
| | | |
|---|---|---|
| *C12N 15/82* | (2006.01) | |
| *C12N 15/63* | (2006.01) | |
| *C12N 15/09* | (2006.01) | |
| *C12N 9/12* | (2006.01) | |

(52) U.S. Cl.
CPC .......... *C12N 15/8261* (2013.01); *C12N 9/1205* (2013.01); *C12N 15/09* (2013.01); *C12N 15/63* (2013.01); *C12N 15/8226* (2013.01); *C12N 15/8241* (2013.01)

(58) Field of Classification Search
None
See application file for complete search history.

(56) References Cited

U.S. PATENT DOCUMENTS

2003/0172402 A1  9/2003  Eriksson et al.
2008/0058510 A1  3/2008  Arruda et al.

FOREIGN PATENT DOCUMENTS

| EP | 1230345 | 6/2008 |
|---|---|---|
| WO | 0215675 | 2/2002 |
| WO | WO-03/000898 A1 | 1/2003 |
| WO | WO 2005/096805 A2 | 10/2005 |

OTHER PUBLICATIONS

Bowie et al, Science 247:1306-1310, 1990.*
McConnell et al, Nature 411 (6838):709-713, 2001.*
He et al (1999, Plant Molecular Biology 39:1189-1196).*
Bruce D. Kohorn et al., "An *Arabidopsis* cell wall-associated kinase required for invertase activity and cell growth", The Plant Journal (2006) vol. 46, No. 2, pp. 307-316.
David Lally et al., "Antisense Expression of a Cell Wall-associated Protein Kinase, WAK4, Inhibits Cell Elongation and Alters Morphology", The Plant Cell, vol. 13, No. 6, Jun. 2001, pp. 1317-1331.
Mayandi Sivaguru et al., "Aluminum-Induced Gene Expression and Protein Localization of a Cell Wall-Associated Receptor Kinase in *Arabidopsis*", Plant Physiology, Aug. 2003, vol. 132, No. 4, pp. 2256-2266.
Supplementary European Search Report EP 07845482.4 dated Jun. 1, 2010.
International Search Report PCT/BR2007/000357 dated May 8, 2008.
Maria E. Eriksson et al., "Increased gibberellin biosynthesis in transgenic trees promotes growth, biomass production and xylem fiber length", Nature Biotechnology, vol. 18, Jul. 2000, pp. 784-788.
Kanneganti et al., "RNAi mediated silencing of a wall associated kinase, OsiWAK1 in *Oryza sativa* results in impaired root development and sterility due to anther indehiscence", Physiology and Molecular Biology of Plants, 2011, pp. 65-77, vol. 17 No. 1.
Identification of *Eucalyptus* species by DNA analysis of wood chips, Nippon Paper Industries Co., Ltd. Press Release, Jun. 21, 1999.
Kohorn et al., "Wall-associated kinase 1 (WAK1) is crosslinked in endomembranes, and transport to the cell surface requires correct cell-wall synthesis", Journal of Cell Science, 2006, pp. 2282-2290, vol. 119 No. 11.
Verica et al., "The Cell Wall-Associated Kinase (WAK) and WAK-Like Kinase Gene Family", Plant Physiology, Jun. 2002, pp. 455-459, vol. 129.
Wagner et al., "Wall-Associated Kinases Are Expressed throughout Plant Development and Are Required for Cell Expansion", The Plant Cell, Feb. 2001, pp. 303-318, vol. 13.

* cited by examiner

*Primary Examiner* — Stuart F Baum
(74) *Attorney, Agent, or Firm* — Arent Fox LLP

(57) ABSTRACT

Nucleic acid constructs and methods are disclosed for modifying fiber length, plant height, and/or plant biomass in plant tissues. Plants are genetically engineered with constructs encoding an *Arabidopsis thaliana* wall-associated kinase gene, which alters fiber length and/or plant height when overexpressed under the control of a cambium/xylem preferred promoter. Plant transformants harboring a wall-associated kinase gene show increased fiber length, a trait that is thought to improve woody trees for pulping and papermaking.

19 Claims, 5 Drawing Sheets

SEQUENCE LISTING

```
<160> NUMBER OF SEQ ID NOS: 12

<210> SEQ ID NO 1
<211> LENGTH: 2217
<212> TYPE: DNA
<213> ORGANISM: Arabidopsis thaliana
<220> FEATURE:
<221> NAME/KEY: CDS
<222> LOCATION: (1)..(2214)
<223> OTHER INFORMATION: Wall-associated kinase 4, cDNA, complete CD
```

<400> SEQUENCE: 1

```
atg aaa gtg cag cgt ctg ttc tta gta gct att ttc tgc ctc tct tat      48
Met Lys Val Gln Arg Leu Phe Leu Val Ala Ile Phe Cys Leu Ser Tyr
1               5                   10                  15 atg cag ctg gtc aag ggg caa acc ttg cct cgt tgc ccc gaa aaa tgt      96
Met Gln Leu Val Lys Gly Gln Thr Leu Pro Arg Cys Pro Glu Lys Cys
            20                  25                  30 ggc aac gtt aca ctt gag tac cct ttt ggc ttt tct cca ggt tgt tgg     144
Gly Asn Val Thr Leu Glu Tyr Pro Phe Gly Phe Ser Pro Gly Cys Trp
        35                  40                  45 cgt gcc gaa gat cct agt ttc aat ctc agt tgt gtg aac gag aat cta     192
Arg Ala Glu Asp Pro Ser Phe Asn Leu Ser Cys Val Asn Glu Asn Leu
    50                  55                  60 ttc tat aag ggc ctt gaa gtg gtc gaa ata tct cac agc agc cag tta     240
Phe Tyr Lys Gly Leu Glu Val Val Glu Ile Ser His Ser Ser Gln Leu
65                  70                  75                  80 cgc gtc cta tat cct gca tcc tac att tgc tac aac agc aaa gga aag     288
Arg Val Leu Tyr Pro Ala Ser Tyr Ile Cys Tyr Asn Ser Lys Gly Lys
                85                  90                  95 ttc gct aaa ggg act tac tac tgg agt aat cta ggt aat ttg act ctc     336
Phe Ala Lys Gly Thr Tyr Tyr Trp Ser Asn Leu Gly Asn Leu Thr Leu
            100                 105                 110 tcc ggc aac aac acg att act gca tta ggc tgt aac tcg tac gct ttt     384
Ser Gly Asn Asn Thr Ile Thr Ala Leu Gly Cys Asn Ser Tyr Ala Phe
        115                 120                 125 gtg tcc tct aat gga act cga aga aac tca gtt gga tgc ata tca gca     432
Val Ser Ser Asn Gly Thr Arg Arg Asn Ser Val Gly Cys Ile Ser Ala
    130                 135                 140 tgt gat gct ctt tcc cat gaa gca aat gga gaa tgt aat ggt gaa ggc     480
Cys Asp Ala Leu Ser His Glu Ala Asn Gly Glu Cys Asn Gly Glu Gly
145                 150                 155                 160 tgc tgc cag aac ccc gtc cct gca ggg aac aat tgg tta ata gtc aga     528
Cys Cys Gln Asn Pro Val Pro Ala Gly Asn Asn Trp Leu Ile Val Arg
                165                 170                 175 tca tat cgc ttt gac aac gac acg tca gtg caa cct atc tct gag ggt     576
Ser Tyr Arg Phe Asp Asn Asp Thr Ser Val Gln Pro Ile Ser Glu Gly
            180                 185                 190 caa tgc atc tac gcc ttt ctc gtt gaa aat ggc aag ttt aag tac aat     624
Gln Cys Ile Tyr Ala Phe Leu Val Glu Asn Gly Lys Phe Lys Tyr Asn
        195                 200                 205 gct tcg gac aaa tat tct tat ctg cag aat agg aat gtg ggg ttt cct     672
Ala Ser Asp Lys Tyr Ser Tyr Leu Gln Asn Arg Asn Val Gly Phe Pro
    210                 215                 220 gtg gtc ttg gat tgg tct att agg gga gag aca tgt ggg caa gtt gga     720
Val Val Leu Asp Trp Ser Ile Arg Gly Glu Thr Cys Gly Gln Val Gly
225                 230                 235                 240 gaa aag aaa tgc ggt gtg aat ggc ata tgt tcc aat tct gct agt ggg     768
Glu Lys Lys Cys Gly Val Asn Gly Ile Cys Ser Asn Ser Ala Ser Gly
                245                 250                 255 atc ggg tat aca tgc aaa tgc aaa gga ggt ttc cag ggg aat cca tat     816
Ile Gly Tyr Thr Cys Lys Cys Lys Gly Gly Phe Gln Gly Asn Pro Tyr
            260                 265                 270 ctt caa aac ggt tgc caa gac atc aat gag tgt act act gct aat cct     864
Leu Gln Asn Gly Cys Gln Asp Ile Asn Glu Cys Thr Thr Ala Asn Pro
        275                 280                 285 atc cat aaa cat aac tgc tcg ggt gac agc acc tgt gaa aac aag ttg     912
Ile His Lys His Asn Cys Ser Gly Asp Ser Thr Cys Glu Asn Lys Leu
    290                 295                 300
```

```
gga cac ttc cgt tgt aat tgt cga tct cgt tac gaa tta aat acc acc    960
Gly His Phe Arg Cys Asn Cys Arg Ser Arg Tyr Glu Leu Asn Thr Thr
305             310                 315                 320 act aat acc tgc aaa cct aaa ggc aat cct gaa tac gtt gaa tgg act   1008
Thr Asn Thr Cys Lys Pro Lys Gly Asn Pro Glu Tyr Val Glu Trp Thr
                325                 330                 335 aca att gtt ctt gga acc act atc ggc ttc ttg gtc att ctg ctt gcc  1056
Thr Ile Val Leu Gly Thr Thr Ile Gly Phe Leu Val Ile Leu Leu Ala
        340                 345                 350 att agc tgt ata gaa cat aaa atg aag aac acc aag gac acc gag ctc  1104
Ile Ser Cys Ile Glu His Lys Met Lys Asn Thr Lys Asp Thr Glu Leu
            355                 360                 365 cga caa caa ttc ttc gag caa aat ggt ggc ggc atg ttg atg cag cga  1152
Arg Gln Gln Phe Phe Glu Gln Asn Gly Gly Gly Met Leu Met Gln Arg
        370                 375                 380 ctc tca gga gca ggg cca tca aat gtt gat gtc aaa atc ttc act gag  1200
Leu Ser Gly Ala Gly Pro Ser Asn Val Asp Val Lys Ile Phe Thr Glu
385                 390                 395                 400 gaa gga atg aag gaa gca act gat ggt tat gat gag aac aga atc ttg  1248
Glu Gly Met Lys Glu Ala Thr Asp Gly Tyr Asp Glu Asn Arg Ile Leu
                405                 410                 415 ggc cag gga ggc caa gga aca gtc tac aaa ggt ata tta ccg gac aac  1296
Gly Gln Gly Gly Gln Gly Thr Val Tyr Lys Gly Ile Leu Pro Asp Asn
            420                 425                 430 tcc ata gtt gct ata aag aaa gct cgg ctt gga gac aat agc caa gta  1344
Ser Ile Val Ala Ile Lys Lys Ala Arg Leu Gly Asp Asn Ser Gln Val
        435                 440                 445 gag cag ttc atc aat gaa gtg ctt gtg ctt tca caa atc aac cat agg  1392
Glu Gln Phe Ile Asn Glu Val Leu Val Leu Ser Gln Ile Asn His Arg
    450                 455                 460 aac gtg gtc aag ctc ttg ggc tgc tgt cta gag act gaa gtt ccc ttg  1440
Asn Val Val Lys Leu Leu Gly Cys Cys Leu Glu Thr Glu Val Pro Leu
465                 470                 475                 480 ttg gtc tat gag ttc att tcc agt ggg acc ctt ttc gat cac tta cac  1488
Leu Val Tyr Glu Phe Ile Ser Ser Gly Thr Leu Phe Asp His Leu His
                485                 490                 495 ggt tct atg ttt gat tct tct cta aca tgg gaa cat cgt ttg aga atg  1536
Gly Ser Met Phe Asp Ser Ser Leu Thr Trp Glu His Arg Leu Arg Met
            500                 505                 510 gct gta gaa ata gct gga act ctt gct tat ctt cac tcc tct gct tct  1584
Ala Val Glu Ile Ala Gly Thr Leu Ala Tyr Leu His Ser Ser Ala Ser
        515                 520                 525 ata cca atc atc cat cgc gat atc aaa act gca aat att ctt ctg gat  1632
Ile Pro Ile Ile His Arg Asp Ile Lys Thr Ala Asn Ile Leu Leu Asp
    530                 535                 540 gaa aac tta act gca aaa gta gct gac ttt ggt gct tca agg ctg ata  1680
Glu Asn Leu Thr Ala Lys Val Ala Asp Phe Gly Ala Ser Arg Leu Ile
545                 550                 555                 560 cca atg gat aaa gaa gac ctc gca act atg gtg caa gga act cta ggt  1728
Pro Met Asp Lys Glu Asp Leu Ala Thr Met Val Gln Gly Thr Leu Gly
                565                 570                 575 tac cta gac cca gaa tat tac aac aca ggg ttg cta aac gaa aag agc  1776
Tyr Leu Asp Pro Glu Tyr Tyr Asn Thr Gly Leu Leu Asn Glu Lys Ser
            580                 585                 590 gat gtt tat agc ttt ggg gta gtc cta atg gaa ctg tta tca ggt caa  1824
Asp Val Tyr Ser Phe Gly Val Val Leu Met Glu Leu Leu Ser Gly Gln
        595                 600                 605 aag gca ttg tgc ttt gaa agg cca cag act tca aaa cat ata gtg agt  1872
Lys Ala Leu Cys Phe Glu Arg Pro Gln Thr Ser Lys His Ile Val Ser
    610                 615                 620
```

```
tac ttt gcc tca gcc acg aaa gag aat agg ttg cac gag att att gat    1920
Tyr Phe Ala Ser Ala Thr Lys Glu Asn Arg Leu His Glu Ile Ile Asp
625                 630                 635                 640 ggc caa gtg atg aac gag aat aat cag agg gag atc cag aaa gct gca    1968
Gly Gln Val Met Asn Glu Asn Asn Gln Arg Glu Ile Gln Lys Ala Ala
                645                 650                 655 aga att gct gtt gag tgt aca aga ttg acg gga gaa gaa agg cca ggg    2016
Arg Ile Ala Val Glu Cys Thr Arg Leu Thr Gly Glu Glu Arg Pro Gly
            660                 665                 670 atg aag gaa gta gct gca gag ctt gag gcc ttg aga gtc aca aaa acc    2064
Met Lys Glu Val Ala Ala Glu Leu Glu Ala Leu Arg Val Thr Lys Thr
        675                 680                 685 aaa cat aag tgg tca gat gag tat cct gaa cag gag gat act gag cac    2112
Lys His Lys Trp Ser Asp Glu Tyr Pro Glu Gln Glu Asp Thr Glu His
690                 695                 700 ttg gtt ggt gtt caa aaa tta tca gca caa ggc gaa acc agc agc agc    2160
Leu Val Gly Val Gln Lys Leu Ser Ala Gln Gly Glu Thr Ser Ser Ser
705                 710                 715                 720 att ggc tat gat agt atc agg aat gta gca ata ctg gac att gaa gca    2208
Ile Gly Tyr Asp Ser Ile Arg Asn Val Ala Ile Leu Asp Ile Glu Ala
                725                 730                 735 ggc cgc tga                                                         2217
Gly Arg <210> SEQ ID NO 2
<211> LENGTH: 738
<212> TYPE: PRT
<213> ORGANISM: Arabidopsis thaliana

<400> SEQUENCE: 2

Met Lys Val Gln Arg Leu Phe Leu Val Ala Ile Phe Cys Leu Ser Tyr
1               5                   10                  15

Met Gln Leu Val Lys Gly Gln Thr Leu Pro Arg Cys Pro Glu Lys Cys
            20                  25                  30

Gly Asn Val Thr Leu Glu Tyr Pro Phe Gly Phe Ser Pro Gly Cys Trp
        35                  40                  45

Arg Ala Glu Asp Pro Ser Phe Asn Leu Ser Cys Val Asn Glu Asn Leu
    50                  55                  60

Phe Tyr Lys Gly Leu Glu Val Val Glu Ile Ser His Ser Ser Gln Leu
65                  70                  75                  80

Arg Val Leu Tyr Pro Ala Ser Tyr Ile Cys Tyr Asn Ser Lys Gly Lys
                85                  90                  95

Phe Ala Lys Gly Thr Tyr Tyr Trp Ser Asn Leu Gly Asn Leu Thr Leu
            100                 105                 110

Ser Gly Asn Asn Thr Ile Thr Ala Leu Gly Cys Asn Ser Tyr Ala Phe
        115                 120                 125

Val Ser Ser Asn Gly Thr Arg Arg Asn Ser Val Gly Cys Ile Ser Ala
    130                 135                 140

Cys Asp Ala Leu Ser His Glu Ala Asn Gly Glu Cys Asn Gly Glu Gly
145                 150                 155                 160

Cys Cys Gln Asn Pro Val Pro Ala Gly Asn Asn Trp Leu Ile Val Arg
                165                 170                 175

Ser Tyr Arg Phe Asp Asn Asp Thr Ser Val Gln Pro Ile Ser Glu Gly
            180                 185                 190

Gln Cys Ile Tyr Ala Phe Leu Val Glu Asn Gly Lys Phe Lys Tyr Asn
        195                 200                 205
```

-continued

```
Ala Ser Asp Lys Tyr Ser Tyr Leu Gln Asn Arg Asn Val Gly Phe Pro
    210             215                 220
Val Val Leu Asp Trp Ser Ile Arg Gly Glu Thr Cys Gly Gln Val Gly
225             230                 235                 240
Glu Lys Lys Cys Gly Val Asn Gly Ile Cys Ser Asn Ser Ala Ser Gly
                245                 250                 255
Ile Gly Tyr Thr Cys Lys Cys Lys Gly Gly Phe Gln Gly Asn Pro Tyr
            260                 265                 270
Leu Gln Asn Gly Cys Gln Asp Ile Asn Glu Cys Thr Thr Ala Asn Pro
        275                 280                 285
Ile His Lys His Asn Cys Ser Gly Asp Ser Thr Cys Glu Asn Lys Leu
    290                 295                 300
Gly His Phe Arg Cys Asn Cys Arg Ser Arg Tyr Glu Leu Asn Thr Thr
305                 310                 315                 320
Thr Asn Thr Cys Lys Pro Lys Gly Asn Pro Glu Tyr Val Glu Trp Thr
                325                 330                 335
Thr Ile Val Leu Gly Thr Thr Ile Gly Phe Leu Val Ile Leu Leu Ala
            340                 345                 350
Ile Ser Cys Ile Glu His Lys Met Lys Asn Thr Lys Asp Thr Glu Leu
        355                 360                 365
Arg Gln Gln Phe Phe Glu Gln Asn Gly Gly Gly Met Leu Met Gln Arg
    370                 375                 380
Leu Ser Gly Ala Gly Pro Ser Asn Val Asp Val Lys Ile Phe Thr Glu
385                 390                 395                 400
Glu Gly Met Lys Glu Ala Thr Asp Gly Tyr Asp Glu Asn Arg Ile Leu
                405                 410                 415
Gly Gln Gly Gly Gln Gly Thr Val Tyr Lys Gly Ile Leu Pro Asp Asn
            420                 425                 430
Ser Ile Val Ala Ile Lys Lys Ala Arg Leu Gly Asp Asn Ser Gln Val
        435                 440                 445
Glu Gln Phe Ile Asn Glu Val Leu Val Leu Ser Gln Ile Asn His Arg
    450                 455                 460
Asn Val Val Lys Leu Leu Gly Cys Cys Leu Glu Thr Glu Val Pro Leu
465                 470                 475                 480
Leu Val Tyr Glu Phe Ile Ser Ser Gly Thr Leu Phe Asp His Leu His
                485                 490                 495
Gly Ser Met Phe Asp Ser Ser Leu Thr Trp Glu His Arg Leu Arg Met
            500                 505                 510
Ala Val Glu Ile Ala Gly Thr Leu Ala Tyr Leu His Ser Ser Ala Ser
        515                 520                 525
Ile Pro Ile Ile His Arg Asp Ile Lys Thr Ala Asn Ile Leu Leu Asp
    530                 535                 540
Glu Asn Leu Thr Ala Lys Val Ala Asp Phe Gly Ala Ser Arg Leu Ile
545                 550                 555                 560
Pro Met Asp Lys Glu Asp Leu Ala Thr Met Val Gln Gly Thr Leu Gly
                565                 570                 575
Tyr Leu Asp Pro Glu Tyr Tyr Asn Thr Gly Leu Leu Asn Glu Lys Ser
            580                 585                 590
Asp Val Tyr Ser Phe Gly Val Leu Met Glu Leu Leu Ser Gly Gln
        595                 600                 605
Lys Ala Leu Cys Phe Glu Arg Pro Gln Thr Ser Lys His Ile Val Ser
    610                 615                 620
Tyr Phe Ala Ser Ala Thr Lys Glu Asn Arg Leu His Glu Ile Ile Asp
```

```
                625                 630                 635                 640
Gly Gln Val Met Asn Glu Asn Gln Arg Glu Ile Gln Lys Ala Ala
                    645                 650                 655

Arg Ile Ala Val Glu Cys Thr Arg Leu Thr Gly Glu Glu Arg Pro Gly
                660                 665                 670

Met Lys Glu Val Ala Ala Glu Leu Glu Ala Leu Arg Val Thr Lys Thr
                675                 680                 685

Lys His Lys Trp Ser Asp Glu Tyr Pro Glu Gln Glu Asp Thr Glu His
            690                 695                 700

Leu Val Gly Val Gln Lys Leu Ser Ala Gln Gly Glu Thr Ser Ser Ser
705                 710                 715                 720

Ile Gly Tyr Asp Ser Ile Arg Asn Val Ala Ile Leu Asp Ile Glu Ala
                    725                 730                 735

Gly Arg

<210> SEQ ID NO 3
<211> LENGTH: 2208
<212> TYPE: DNA
<213> ORGANISM: Arabidopsis thaliana
<220> FEATURE:
<221> NAME/KEY: CDS
<222> LOCATION: (1)..(2205)
<223> OTHER INFORMATION: Wall-associated kinase 1, cDNA, complete CDS

<400> SEQUENCE: 3 atg aag gtg cag gag ggt ttg ttc ttg gtg gct att ttc ttc tcc ctt      48
Met Lys Val Gln Glu Gly Leu Phe Leu Val Ala Ile Phe Phe Ser Leu
1               5                   10                  15 gcg tgt acg cag ctg gtg aag ggg caa cat caa cct ggt gag aat tgc      96
Ala Cys Thr Gln Leu Val Lys Gly Gln His Gln Pro Gly Glu Asn Cys
                20                  25                  30 caa aat aaa tgt ggc aac atc aca ata gag tac cct ttt ggc att tct     144
Gln Asn Lys Cys Gly Asn Ile Thr Ile Glu Tyr Pro Phe Gly Ile Ser
            35                  40                  45 tca ggt tgt tac tat ccc gga aat gaa agt ttc agt atc acc tgt aag     192
Ser Gly Cys Tyr Tyr Pro Gly Asn Glu Ser Phe Ser Ile Thr Cys Lys
        50                  55                  60 gaa gat agg cca cat gtc tta agc gac att gaa gtg gca aac ttt aat     240
Glu Asp Arg Pro His Val Leu Ser Asp Ile Glu Val Ala Asn Phe Asn
65                  70                  75                  80 cac agc ggc cag cta caa gtt ctg ctt aat cga tcc tct act tgc tac     288
His Ser Gly Gln Leu Gln Val Leu Leu Asn Arg Ser Ser Thr Cys Tyr
                85                  90                  95 gac gag caa gga aaa aaa act gag gag gac agt tct ttt aca ctg gaa     336
Asp Glu Gln Gly Lys Lys Thr Glu Glu Asp Ser Ser Phe Thr Leu Glu
                100                 105                 110 aat tta tct ctt tcc gcc aac aac aag tta act gca gta ggc tgt aac     384
Asn Leu Ser Leu Ser Ala Asn Asn Lys Leu Thr Ala Val Gly Cys Asn
            115                 120                 125 gct tta tca ctt ctg gac act ttt gga atg caa aac tac tca act gca     432
Ala Leu Ser Leu Leu Asp Thr Phe Gly Met Gln Asn Tyr Ser Thr Ala
        130                 135                 140 tgc ttg tca tta tgc gat tct ccc cca gag gct gat gga gaa tgt aat     480
Cys Leu Ser Leu Cys Asp Ser Pro Pro Glu Ala Asp Gly Glu Cys Asn
145                 150                 155                 160 ggt aga ggt tgc tgc aga gtc gac gtt tct gcc ccg ttg gat agc tat     528
Gly Arg Gly Cys Cys Arg Val Asp Val Ser Ala Pro Leu Asp Ser Tyr
                165                 170                 175 aca ttc gaa act aca tca ggt cgc atc aag cac atg act tct ttt cac     576
```

```
Thr Phe Glu Thr Thr Ser Gly Arg Ile Lys His Met Thr Ser Phe His
            180                 185                 190 gac ttt agt cct tgc acc tac gct ttt ctc gtt gaa gat gat aag ttc      624
Asp Phe Ser Pro Cys Thr Tyr Ala Phe Leu Val Glu Asp Asp Lys Phe
        195                 200                 205 aac ttc agt tct aca gaa gat ctt ctg aat ctg cga aat gtc atg agg      672
Asn Phe Ser Ser Thr Glu Asp Leu Leu Asn Leu Arg Asn Val Met Arg
    210                 215                 220 ttc cct gtg tta cta gat tgg tct gtt gga aat cag aca tgc gag caa      720
Phe Pro Val Leu Leu Asp Trp Ser Val Gly Asn Gln Thr Cys Glu Gln
225                 230                 235                 240 gtt gga agc aca agc ata tgc ggt ggg aac agc act tgt ctc gat tct      768
Val Gly Ser Thr Ser Ile Cys Gly Gly Asn Ser Thr Cys Leu Asp Ser
                245                 250                 255 act cct aga aac ggg tat atc tgc aga tgc aat gaa ggc ttt gat ggg      816
Thr Pro Arg Asn Gly Tyr Ile Cys Arg Cys Asn Glu Gly Phe Asp Gly
            260                 265                 270 aat cca tac ctt tca gct ggt tgc caa gac gtc aat gag tgt act act      864
Asn Pro Tyr Leu Ser Ala Gly Cys Gln Asp Val Asn Glu Cys Thr Thr
        275                 280                 285 agt agt act atc cat aga cat aac tgt tcg gat ccc aaa acc tgt aga      912
Ser Ser Thr Ile His Arg His Asn Cys Ser Asp Pro Lys Thr Cys Arg
    290                 295                 300 aac aag gtt gga ggc ttc tat tgt aag tgt caa tct ggt tac cgc tta      960
Asn Lys Val Gly Gly Phe Tyr Cys Lys Cys Gln Ser Gly Tyr Arg Leu
305                 310                 315                 320 gat acc acc act atg agc tgc aag cgt aaa gag ttt gca tgg act aca     1008
Asp Thr Thr Thr Met Ser Cys Lys Arg Lys Glu Phe Ala Trp Thr Thr
                325                 330                 335 att ctt ctt gta acc acc atc ggc ttc ttg gtc att ctg ctt ggc gtt     1056
Ile Leu Leu Val Thr Thr Ile Gly Phe Leu Val Ile Leu Leu Gly Val
            340                 345                 350 gcc tgt ata caa cag aga atg aag cac ctg aag gac acc aag ctc cga     1104
Ala Cys Ile Gln Gln Arg Met Lys His Leu Lys Asp Thr Lys Leu Arg
        355                 360                 365 gaa caa ttc ttc gag caa aat ggt ggc ggc atg ttg aca caa cga ctc     1152
Glu Gln Phe Phe Glu Gln Asn Gly Gly Gly Met Leu Thr Gln Arg Leu
    370                 375                 380 tca gga gca ggg ccg tca aat gtt gat gtc aaa atc ttt act gag gat     1200
Ser Gly Ala Gly Pro Ser Asn Val Asp Val Lys Ile Phe Thr Glu Asp
385                 390                 395                 400 ggc atg aag aaa gca aca aat ggt tat gct gag agc agg atc ctg ggt     1248
Gly Met Lys Lys Ala Thr Asn Gly Tyr Ala Glu Ser Arg Ile Leu Gly
                405                 410                 415 cag ggt ggc caa gga aca gtg tac aaa ggg ata ttg ccg gac aac tcc     1296
Gln Gly Gly Gln Gly Thr Val Tyr Lys Gly Ile Leu Pro Asp Asn Ser
            420                 425                 430 ata gtt gct ata aag aaa gcc cga ctt gga gac agt agc caa gta gag     1344
Ile Val Ala Ile Lys Lys Ala Arg Leu Gly Asp Ser Ser Gln Val Glu
        435                 440                 445 cag ttc atc aat gaa gtg ctc gtg ctt tca caa atc aac cat agg aac     1392
Gln Phe Ile Asn Glu Val Leu Val Leu Ser Gln Ile Asn His Arg Asn
    450                 455                 460 gta gtc aag ctc ttg ggc tgc tgt cta gag act gaa gtt ccc ttg ttg     1440
Val Val Lys Leu Leu Gly Cys Cys Leu Glu Thr Glu Val Pro Leu Leu
465                 470                 475                 480 gtc tat gag ttc atc acc aat ggc acc ctt ttc gat cac ttg cat ggt     1488
Val Tyr Glu Phe Ile Thr Asn Gly Thr Leu Phe Asp His Leu His Gly
                485                 490                 495
```

```
tcc atg att gat tct tcg ctt aca tgg gaa cac cgt ctg aag ata gca    1536
Ser Met Ile Asp Ser Ser Leu Thr Trp Glu His Arg Leu Lys Ile Ala
        500                 505                 510 ata gaa gtc gct gga act ctt gca tat ctt cac tcc tct gct tct att    1584
Ile Glu Val Ala Gly Thr Leu Ala Tyr Leu His Ser Ser Ala Ser Ile
    515                 520                 525 cca atc atc cat cgg gat atc aaa act gca aat att ctt ctg gat gta    1632
Pro Ile Ile His Arg Asp Ile Lys Thr Ala Asn Ile Leu Leu Asp Val
530                 535                 540 aac tta act gca aaa gta gct gac ttt ggt gct tca agg ctg ata cca    1680
Asn Leu Thr Ala Lys Val Ala Asp Phe Gly Ala Ser Arg Leu Ile Pro
545                 550                 555                 560 atg gat aaa gaa gag ctc gaa act atg gtg caa ggc act cta ggt tac    1728
Met Asp Lys Glu Glu Leu Glu Thr Met Val Gln Gly Thr Leu Gly Tyr
                565                 570                 575 cta gac cca gaa tat tac aac aca ggg ttg tta aac gaa aag agc gat    1776
Leu Asp Pro Glu Tyr Tyr Asn Thr Gly Leu Leu Asn Glu Lys Ser Asp
            580                 585                 590 gtt tat agt ttt ggg gtc gtc cta atg gaa ctg ctc tca ggt caa aag    1824
Val Tyr Ser Phe Gly Val Val Leu Met Glu Leu Leu Ser Gly Gln Lys
        595                 600                 605 gca ttg tgc ttt aaa cgg cca cag tcc tca aaa cat ctg gtg agt tac    1872
Ala Leu Cys Phe Lys Arg Pro Gln Ser Ser Lys His Leu Val Ser Tyr
610                 615                 620 ttt gcg act gcc aca aaa gag aat agg ttg gat gag att att ggc ggc    1920
Phe Ala Thr Ala Thr Lys Glu Asn Arg Leu Asp Glu Ile Ile Gly Gly
625                 630                 635                 640 gaa gtg atg aac gag gat aat ctg aag gag atc cag gaa gct gca aga    1968
Glu Val Met Asn Glu Asp Asn Leu Lys Glu Ile Gln Glu Ala Ala Arg
                645                 650                 655 att gct gca gag tgt aca agg cta atg gga gag gaa agg cca agg atg    2016
Ile Ala Ala Glu Cys Thr Arg Leu Met Gly Glu Glu Arg Pro Arg Met
            660                 665                 670 aaa gaa gta gct gca aag cta gaa gcc ttg agg gtc gaa aaa acc aaa    2064
Lys Glu Val Ala Ala Lys Leu Glu Ala Leu Arg Val Glu Lys Thr Lys
        675                 680                 685 cat aag tgg tcg gat cag tac cct gag gag aat gaa cac ttg att ggt    2112
His Lys Trp Ser Asp Gln Tyr Pro Glu Glu Asn Glu His Leu Ile Gly
690                 695                 700 ggt cac atc ttg tca gca caa ggc gaa acc agt agc agc att ggc tat    2160
Gly His Ile Leu Ser Ala Gln Gly Glu Thr Ser Ser Ser Ile Gly Tyr
705                 710                 715                 720 gac agc atc aag aat gta gca ata ttg gac att gaa act ggc cgc tga    2208
Asp Ser Ile Lys Asn Val Ala Ile Leu Asp Ile Glu Thr Gly Arg
                725                 730                 735

<210> SEQ ID NO 4
<211> LENGTH: 735
<212> TYPE: PRT
<213> ORGANISM: Arabidopsis thaliana

<400> SEQUENCE: 4

Met Lys Val Gln Glu Gly Leu Phe Leu Val Ala Ile Phe Phe Ser Leu
1               5                   10                  15

Ala Cys Thr Gln Leu Val Lys Gly Gln His Gln Pro Gly Glu Asn Cys
            20                  25                  30

Gln Asn Lys Cys Gly Asn Ile Thr Ile Glu Tyr Pro Phe Gly Ile Ser
        35                  40                  45

Ser Gly Cys Tyr Tyr Pro Gly Asn Glu Ser Phe Ser Ile Thr Cys Lys
    50                  55                  60
```

-continued

```
Glu Asp Arg Pro His Val Leu Ser Asp Ile Glu Val Ala Asn Phe Asn
65                  70                  75                  80

His Ser Gly Gln Leu Gln Val Leu Leu Asn Arg Ser Ser Thr Cys Tyr
            85                  90                  95

Asp Glu Gln Gly Lys Lys Thr Glu Glu Asp Ser Ser Phe Thr Leu Glu
            100                 105                 110

Asn Leu Ser Leu Ser Ala Asn Asn Lys Leu Thr Ala Val Gly Cys Asn
            115                 120                 125

Ala Leu Ser Leu Leu Asp Thr Phe Gly Met Gln Asn Tyr Ser Thr Ala
130                 135                 140

Cys Leu Ser Leu Cys Asp Ser Pro Glu Ala Asp Gly Glu Cys Asn
145                 150                 155                 160

Gly Arg Gly Cys Cys Arg Val Asp Val Ser Ala Pro Leu Asp Ser Tyr
                165                 170                 175

Thr Phe Glu Thr Thr Ser Gly Arg Ile Lys His Met Thr Ser Phe His
            180                 185                 190

Asp Phe Ser Pro Cys Thr Tyr Ala Phe Leu Val Glu Asp Asp Lys Phe
            195                 200                 205

Asn Phe Ser Ser Thr Glu Asp Leu Leu Asn Leu Arg Asn Val Met Arg
210                 215                 220

Phe Pro Val Leu Leu Asp Trp Ser Val Gly Asn Gln Thr Cys Glu Gln
225                 230                 235                 240

Val Gly Ser Thr Ser Ile Cys Gly Gly Asn Ser Thr Cys Leu Asp Ser
                245                 250                 255

Thr Pro Arg Asn Gly Tyr Ile Cys Arg Cys Asn Glu Gly Phe Asp Gly
            260                 265                 270

Asn Pro Tyr Leu Ser Ala Gly Cys Gln Asp Val Asn Glu Cys Thr Thr
            275                 280                 285

Ser Ser Thr Ile His Arg His Asn Cys Ser Asp Pro Lys Thr Cys Arg
290                 295                 300

Asn Lys Val Gly Gly Phe Tyr Cys Lys Cys Gln Ser Gly Tyr Arg Leu
305                 310                 315                 320

Asp Thr Thr Thr Met Ser Cys Lys Arg Lys Glu Phe Ala Trp Thr Thr
                325                 330                 335

Ile Leu Leu Val Thr Thr Ile Gly Phe Leu Val Ile Leu Leu Gly Val
            340                 345                 350

Ala Cys Ile Gln Gln Arg Met Lys His Leu Lys Asp Thr Lys Leu Arg
            355                 360                 365

Glu Gln Phe Phe Glu Gln Asn Gly Gly Met Leu Thr Gln Arg Leu
370                 375                 380

Ser Gly Ala Gly Pro Ser Asn Val Asp Val Lys Ile Phe Thr Glu Asp
385                 390                 395                 400

Gly Met Lys Lys Ala Thr Asn Gly Tyr Ala Glu Ser Arg Ile Leu Gly
                405                 410                 415

Gln Gly Gly Gln Gly Thr Val Tyr Lys Gly Ile Leu Pro Asp Asn Ser
            420                 425                 430

Ile Val Ala Ile Lys Lys Ala Arg Leu Gly Asp Ser Ser Gln Val Glu
            435                 440                 445

Gln Phe Ile Asn Glu Val Leu Val Leu Ser Gln Ile Asn His Arg Asn
            450                 455                 460

Val Val Lys Leu Leu Gly Cys Cys Leu Glu Thr Glu Val Pro Leu Leu
465                 470                 475                 480
```

```
Val Tyr Glu Phe Ile Thr Asn Gly Thr Leu Phe Asp His Leu His Gly
                485                 490                 495

Ser Met Ile Asp Ser Ser Leu Thr Trp Glu His Arg Leu Lys Ile Ala
            500                 505                 510

Ile Glu Val Ala Gly Thr Leu Ala Tyr Leu His Ser Ser Ala Ser Ile
            515                 520                 525

Pro Ile Ile His Arg Asp Ile Lys Thr Ala Asn Ile Leu Leu Asp Val
            530                 535                 540

Asn Leu Thr Ala Lys Val Ala Asp Phe Gly Ala Ser Arg Leu Ile Pro
545                 550                 555                 560

Met Asp Lys Glu Glu Leu Glu Thr Met Val Gln Gly Thr Leu Gly Tyr
                565                 570                 575

Leu Asp Pro Glu Tyr Tyr Asn Thr Gly Leu Leu Asn Glu Lys Ser Asp
            580                 585                 590

Val Tyr Ser Phe Gly Val Val Leu Met Glu Leu Leu Ser Gly Gln Lys
            595                 600                 605

Ala Leu Cys Phe Lys Arg Pro Gln Ser Ser Lys His Leu Val Ser Tyr
            610                 615                 620

Phe Ala Thr Ala Thr Lys Glu Asn Arg Leu Asp Glu Ile Ile Gly Gly
625                 630                 635                 640

Glu Val Met Asn Glu Asp Asn Leu Lys Glu Ile Gln Glu Ala Ala Arg
                645                 650                 655

Ile Ala Ala Glu Cys Thr Arg Leu Met Gly Glu Arg Pro Arg Met
            660                 665                 670

Lys Glu Val Ala Ala Lys Leu Glu Ala Leu Arg Val Gly Lys Thr Lys
            675                 680                 685

His Lys Trp Ser Asp Gln Tyr Pro Glu Glu Asn Glu His Leu Ile Gly
            690                 695                 700

Gly His Ile Leu Ser Ala Gln Gly Glu Thr Ser Ser Ile Gly Tyr
705                 710                 715                 720

Asp Ser Ile Lys Asn Val Ala Ile Leu Asp Ile Glu Thr Gly Arg
                725                 730                 735

<210> SEQ ID NO 5
<211> LENGTH: 2199
<212> TYPE: DNA
<213> ORGANISM: Arabidopsis thaliana
<220> FEATURE:
<221> NAME/KEY: CDS
<223> OTHER INFORMATION: Wall-associated kinase 2, cDNA, complete CDS

<400> SEQUENCE: 5 atg aag gta cag gag ggt ttg ttc gtg gtg gct gtt ttc tac ctt gct     48
Met Lys Val Gln Glu Gly Leu Phe Val Val Ala Val Phe Tyr Leu Ala
1               5                   10                  15 tat acg cag cta gtc aag ggg caa cct cgc aag gag tgc caa act aga     96
Tyr Thr Gln Leu Val Lys Gly Gln Pro Arg Lys Glu Cys Gln Thr Arg
                20                  25                  30 tgt ggc aat gtc gca gtt gag tac cct ttt ggt act tct cca ggt tgt    144
Cys Gly Asn Val Ala Val Glu Tyr Pro Phe Gly Thr Ser Pro Gly Cys
            35                  40                  45 tac tat ccc gga gat gaa agt ttc aat ctt act tgc aac gag caa gag    192
Tyr Tyr Pro Gly Asp Glu Ser Phe Asn Leu Thr Cys Asn Glu Gln Glu
        50                  55                  60 aag ctc ttc ttt ggc aac atg cca gtc atc aac atg tct ctc agc ggc    240
Lys Leu Phe Phe Gly Asn Met Pro Val Ile Asn Met Ser Leu Ser Gly
65                  70                  75                  80
```

-continued

| | |
|---|---|
| cag ctt cgt gtt cgg cta gtt aga tcc aga gtt tgc tac gat agt caa<br>Gln Leu Arg Val Arg Leu Val Arg Ser Arg Val Cys Tyr Asp Ser Gln<br>                      85                      90                  95 | 288 |
| gga aaa cag act gac tac att gcc cag cgg acc acc ctg ggt aat ttc<br>Gly Lys Gln Thr Asp Tyr Ile Ala Gln Arg Thr Thr Leu Gly Asn Phe<br>            100                      105                      110 | 336 |
| act ctc tct gaa ctt aac aga ttt act gta gta ggt tgt aac agt tac<br>Thr Leu Ser Glu Leu Asn Arg Phe Thr Val Val Gly Cys Asn Ser Tyr<br>                115                      120                      125 | 384 |
| gca ttt ctc cgc aca tct gga gtt gaa aaa tac tca act gga tgc ata<br>Ala Phe Leu Arg Thr Ser Gly Val Glu Lys Tyr Ser Thr Gly Cys Ile<br>            130                      135                      140 | 432 |
| tca ata tgt gat tct gcc aca acg aaa aac gga tca tgt tct ggt gaa<br>Ser Ile Cys Asp Ser Ala Thr Thr Lys Asn Gly Ser Cys Ser Gly Glu<br>145                      150                      155                      160 | 480 |
| ggt tgc tgc cag atc cct gtc cct aga gga tac tct ttt gtc aga gta<br>Gly Cys Cys Gln Ile Pro Val Pro Arg Gly Tyr Ser Phe Val Arg Val<br>                      165                      170                      175 | 528 |
| aaa cca cat agc ttt cac aac cat cct act gtg cat ctg ttt aat cct<br>Lys Pro His Ser Phe His Asn His Pro Thr Val His Leu Phe Asn Pro<br>            180                      185                      190 | 576 |
| tgc acc tac gcc ttt ctc gtt gaa gat ggt atg ttt gac ttc cat gct<br>Cys Thr Tyr Ala Phe Leu Val Glu Asp Gly Met Phe Asp Phe His Ala<br>                195                      200                      205 | 624 |
| ttg gaa gat ctc aac aat ctg cga aat gtt act acg ttc cct gta gta<br>Leu Glu Asp Leu Asn Asn Leu Arg Asn Val Thr Thr Phe Pro Val Val<br>210                      215                      220 | 672 |
| cta gat tgg tct atc gga gac aag act tgc aaa caa gta gaa tac agg<br>Leu Asp Trp Ser Ile Gly Asp Lys Thr Cys Lys Gln Val Glu Tyr Arg<br>225                      230                      235                      240 | 720 |
| ggc gtg tgt ggt ggt aac agc aca tgt ttc gat tct act ggt gga acc<br>Gly Val Cys Gly Gly Asn Ser Thr Cys Phe Asp Ser Thr Gly Gly Thr<br>                      245                      250                      255 | 768 |
| ggg tat aac tgc aaa tgt tta gaa ggt ttt gag ggg aat cca tac ctt<br>Gly Tyr Asn Cys Lys Cys Leu Glu Gly Phe Glu Gly Asn Pro Tyr Leu<br>            260                      265                      270 | 816 |
| cca aac ggt tgt caa gac atc aat gaa tgt att agt agt aga cat aac<br>Pro Asn Gly Cys Gln Asp Ile Asn Glu Cys Ile Ser Ser Arg His Asn<br>            275                      280                      285 | 864 |
| tgt tcg gag cat agt acc tgt gaa aac acg aag ggg agc ttc aac tgt<br>Cys Ser Glu His Ser Thr Cys Glu Asn Thr Lys Gly Ser Phe Asn Cys<br>            290                      295                      300 | 912 |
| aac tgc cca tct ggt tac cgc aaa gat tcc ctt aat agc tgt act cgt<br>Asn Cys Pro Ser Gly Tyr Arg Lys Asp Ser Leu Asn Ser Cys Thr Arg<br>305                      310                      315                      320 | 960 |
| aaa gtc agg cct gaa tac ttt aga tgg act caa att ttt ctt gga acc<br>Lys Val Arg Pro Glu Tyr Phe Arg Trp Thr Gln Ile Phe Leu Gly Thr<br>                325                      330                      335 | 1008 |
| acc atc ggc ttc tcg gtt atc atg ctt ggg att agc tgt cta caa cag<br>Thr Ile Gly Phe Ser Val Ile Met Leu Gly Ile Ser Cys Leu Gln Gln<br>            340                      345                      350 | 1056 |
| aaa att aag cac cgg aag aac aca gag ctc cga caa aaa ttc ttc gag<br>Lys Ile Lys His Arg Lys Asn Thr Glu Leu Arg Gln Lys Phe Phe Glu<br>                355                      360                      365 | 1104 |
| caa aat ggt gga ggc atg ttg ata cag cga gtc tcg gga gca ggg cca<br>Gln Asn Gly Gly Gly Met Leu Ile Gln Arg Val Ser Gly Ala Gly Pro<br>370                      375                      380 | 1152 |
| tca aat gtt gat gtc aaa atc ttc act gag aaa gga atg aag gaa gca<br>Ser Asn Val Asp Val Lys Ile Phe Thr Glu Lys Gly Met Lys Glu Ala<br>385                      390                      395                      400 | 1200 |

| | | |
|---|---|---|
| act aat ggt tac cat gag agc aga atc ctg ggt cag gga ggc caa gga<br>Thr Asn Gly Tyr His Glu Ser Arg Ile Leu Gly Gln Gly Gly Gln Gly<br>405 410 415 | | 1248 |
| aca gtg tac aaa ggg ata ttg ccg gac aac tcc ata gtt gct ata aag<br>Thr Val Tyr Lys Gly Ile Leu Pro Asp Asn Ser Ile Val Ala Ile Lys<br>420 425 430 | | 1296 |
| aaa gct cgg ctt gga aac cgt agc caa gta gag cag ttc atc aac gaa<br>Lys Ala Arg Leu Gly Asn Arg Ser Gln Val Glu Gln Phe Ile Asn Glu<br>435 440 445 | | 1344 |
| gtg cta gtg ctt tca caa atc aac cat agg aac gtg gtc aag gtc ttg<br>Val Leu Val Leu Ser Gln Ile Asn His Arg Asn Val Val Lys Val Leu<br>450 455 460 | | 1392 |
| ggg tgt tgt tta gag aca gaa gtc ccc ttg ttg gtc tat gag ttc att<br>Gly Cys Cys Leu Glu Thr Glu Val Pro Leu Leu Val Tyr Glu Phe Ile<br>465 470 475 480 | | 1440 |
| aac agt ggt acc ctt ttc gat cac ttg cac ggt tcc ttg tat gat tct<br>Asn Ser Gly Thr Leu Phe Asp His Leu His Gly Ser Leu Tyr Asp Ser<br>485 490 495 | | 1488 |
| tca ctt aca tgg gag cac cgt ctg agg ata gca aca gaa gta gca gga<br>Ser Leu Thr Trp Glu His Arg Leu Arg Ile Ala Thr Glu Val Ala Gly<br>500 505 510 | | 1536 |
| agt ctt gca tat ctt cac tct tct gct tct att cca atc atc cac cga<br>Ser Leu Ala Tyr Leu His Ser Ser Ala Ser Ile Pro Ile Ile His Arg<br>515 520 525 | | 1584 |
| gat atc aag act gct aat att ctc ctg gat aaa aac tta act gca aaa<br>Asp Ile Lys Thr Ala Asn Ile Leu Leu Asp Lys Asn Leu Thr Ala Lys<br>530 535 540 | | 1632 |
| gta gct gac ttt ggt gca tca aga ttg ata ccg atg gat aaa gag cag<br>Val Ala Asp Phe Gly Ala Ser Arg Leu Ile Pro Met Asp Lys Glu Gln<br>545 550 555 560 | | 1680 |
| ctc aca aca ata gtg caa ggc act cta ggt tac cta gac cca gaa tat<br>Leu Thr Thr Ile Val Gln Gly Thr Leu Gly Tyr Leu Asp Pro Glu Tyr<br>565 570 575 | | 1728 |
| tac aac aca ggg ttg tta aac gaa aag agc gat gtt tat agt ttt ggg<br>Tyr Asn Thr Gly Leu Leu Asn Glu Lys Ser Asp Val Tyr Ser Phe Gly<br>580 585 590 | | 1776 |
| gtc gtc cta atg gaa ctg ctc tca ggt caa aag gca ttg tgt ttc gaa<br>Val Val Leu Met Glu Leu Leu Ser Gly Gln Lys Ala Leu Cys Phe Glu<br>595 600 605 | | 1824 |
| aga cca cat tgc cca aaa aat ctt gtg agt tgt ttt gct tct gcc aca<br>Arg Pro His Cys Pro Lys Asn Leu Val Ser Cys Phe Ala Ser Ala Thr<br>610 615 620 | | 1872 |
| aag aat aat agg ttc cat gaa att att gat ggg caa gtg atg aat gag<br>Lys Asn Asn Arg Phe His Glu Ile Ile Asp Gly Gln Val Met Asn Glu<br>625 630 635 640 | | 1920 |
| gat aac cag aga gag atc cag gaa gct gca aga att gct gca gag tgt<br>Asp Asn Gln Arg Glu Ile Gln Glu Ala Ala Arg Ile Ala Ala Glu Cys<br>645 650 655 | | 1968 |
| aca agg cta atg gga gag gaa agg cca agg atg aaa gaa gta gct gca<br>Thr Arg Leu Met Gly Glu Glu Arg Pro Arg Met Lys Glu Val Ala Ala<br>660 665 670 | | 2016 |
| gag tta gag gcc ttg aga gtt aaa aca act aaa tat aag tgg tcg gat<br>Glu Leu Glu Ala Leu Arg Val Lys Thr Thr Lys Tyr Lys Trp Ser Asp<br>675 680 685 | | 2064 |
| cag tat cgt gag aca ggg gag att gaa cac ttg ctc ggc gtt caa atc<br>Gln Tyr Arg Glu Thr Gly Glu Ile Glu His Leu Leu Gly Val Gln Ile<br>690 695 700 | | 2112 |
| ttg tca gca caa ggc gaa acc agt agc agc att ggc tat gac agc atc<br>Leu Ser Ala Gln Gly Glu Thr Ser Ser Ser Ile Gly Tyr Asp Ser Ile | | 2160 |

```
                705                 710                 715                 720
                aga aat gta aca aca ttg gac att gaa gct ggc cgt tga             2199
                Arg Asn Val Thr Thr Leu Asp Ile Glu Ala Gly Arg
                                725                 730
```

<210> SEQ ID NO 6
<211> LENGTH: 732
<212> TYPE: PRT
<213> ORGANISM: Arabidopsis thaliana

<400> SEQUENCE: 6

```
Met Lys Val Gln Glu Gly Leu Phe Val Ala Val Phe Tyr Leu Ala
1               5                   10                  15

Tyr Thr Gln Leu Val Lys Gly Gln Pro Arg Lys Glu Cys Gln Thr Arg
                20                  25                  30

Cys Gly Asn Val Ala Val Glu Tyr Pro Phe Gly Thr Ser Pro Gly Cys
            35                  40                  45

Tyr Tyr Pro Gly Asp Glu Ser Phe Asn Leu Thr Cys Asn Glu Gln Glu
        50                  55                  60

Lys Leu Phe Phe Gly Asn Met Pro Val Ile Asn Met Ser Leu Ser Gly
65                  70                  75                  80

Gln Leu Arg Val Arg Leu Val Arg Ser Arg Val Cys Tyr Asp Ser Gln
                85                  90                  95

Gly Lys Gln Thr Asp Tyr Ile Ala Gln Arg Thr Thr Leu Gly Asn Phe
            100                 105                 110

Thr Leu Ser Glu Leu Asn Arg Phe Thr Val Val Gly Cys Asn Ser Tyr
        115                 120                 125

Ala Phe Leu Arg Thr Ser Gly Val Glu Lys Tyr Ser Thr Gly Cys Ile
    130                 135                 140

Ser Ile Cys Asp Ser Ala Thr Thr Lys Asn Gly Ser Cys Ser Gly Glu
145                 150                 155                 160

Gly Cys Cys Gln Ile Pro Val Pro Arg Gly Tyr Ser Phe Val Arg Val
                165                 170                 175

Lys Pro His Ser Phe His Asn His Pro Thr Val His Leu Phe Asn Pro
            180                 185                 190

Cys Thr Tyr Ala Phe Leu Val Glu Asp Gly Met Phe Asp Phe His Ala
        195                 200                 205

Leu Glu Asp Leu Asn Asn Leu Arg Asn Val Thr Thr Phe Pro Val Val
    210                 215                 220

Leu Asp Trp Ser Ile Gly Asp Lys Thr Cys Lys Gln Val Glu Tyr Arg
225                 230                 235                 240

Gly Val Cys Gly Gly Asn Ser Thr Cys Phe Asp Ser Thr Gly Thr
                245                 250                 255

Gly Tyr Asn Cys Lys Cys Leu Glu Gly Phe Glu Gly Asn Pro Tyr Leu
            260                 265                 270

Pro Asn Gly Cys Gln Asp Ile Asn Glu Cys Ile Ser Ser Arg His Asn
        275                 280                 285

Cys Ser Glu His Ser Thr Cys Glu Asn Thr Lys Gly Ser Phe Asn Cys
    290                 295                 300

Asn Cys Pro Ser Gly Tyr Arg Lys Asp Ser Leu Asn Ser Cys Thr Arg
305                 310                 315                 320

Lys Val Arg Pro Glu Tyr Phe Arg Trp Thr Gln Ile Phe Leu Gly Thr
                325                 330                 335

Thr Ile Gly Phe Ser Val Ile Met Leu Gly Ile Ser Cys Leu Gln Gln
            340                 345                 350
```

```
Lys Ile Lys His Arg Lys Asn Thr Glu Leu Arg Gln Lys Phe Glu
        355                 360                 365

Gln Asn Gly Gly Gly Met Leu Ile Gln Arg Val Ser Gly Ala Gly Pro
370                 375                 380

Ser Asn Val Asp Val Lys Ile Phe Thr Glu Lys Gly Met Lys Glu Ala
385                 390                 395                 400

Thr Asn Gly Tyr His Glu Ser Arg Ile Leu Gly Gln Gly Gln Gly
                405                 410                 415

Thr Val Tyr Lys Gly Ile Leu Pro Asp Asn Ser Ile Val Ala Ile Lys
                420                 425                 430

Lys Ala Arg Leu Gly Asn Arg Ser Gln Val Glu Gln Phe Ile Asn Glu
        435                 440                 445

Val Leu Val Leu Ser Gln Ile Asn His Arg Asn Val Val Lys Val Leu
450                 455                 460

Gly Cys Cys Leu Glu Thr Glu Val Pro Leu Leu Val Tyr Glu Phe Ile
465                 470                 475                 480

Asn Ser Gly Thr Leu Phe Asp His Leu His Gly Ser Leu Tyr Asp Ser
                485                 490                 495

Ser Leu Thr Trp Glu His Arg Leu Arg Ile Ala Thr Glu Val Ala Gly
                500                 505                 510

Ser Leu Ala Tyr Leu His Ser Ser Ala Ser Ile Pro Ile Ile His Arg
        515                 520                 525

Asp Ile Lys Thr Ala Asn Ile Leu Leu Asp Lys Asn Leu Thr Ala Lys
530                 535                 540

Val Ala Asp Phe Gly Ala Ser Arg Leu Ile Pro Met Asp Lys Glu Gln
545                 550                 555                 560

Leu Thr Thr Ile Val Gln Gly Thr Leu Gly Tyr Leu Asp Pro Glu Tyr
                565                 570                 575

Tyr Asn Thr Gly Leu Leu Asn Glu Lys Ser Asp Val Tyr Ser Phe Gly
                580                 585                 590

Val Val Leu Met Glu Leu Leu Ser Gly Gln Lys Ala Leu Cys Phe Glu
        595                 600                 605

Arg Pro His Cys Pro Lys Asn Leu Val Ser Cys Phe Ala Ser Ala Thr
610                 615                 620

Lys Asn Asn Arg Phe His Glu Ile Ile Asp Gly Gln Val Met Asn Glu
625                 630                 635                 640

Asp Asn Gln Arg Glu Ile Gln Glu Ala Ala Arg Ile Ala Ala Glu Cys
                645                 650                 655

Thr Arg Leu Met Gly Glu Glu Arg Pro Arg Met Lys Glu Val Ala Ala
                660                 665                 670

Glu Leu Glu Ala Leu Arg Val Lys Thr Thr Lys Tyr Lys Trp Ser Asp
        675                 680                 685

Gln Tyr Arg Glu Thr Gly Glu Ile Glu His Leu Leu Gly Val Gln Ile
690                 695                 700

Leu Ser Ala Gln Gly Glu Thr Ser Ser Ser Ile Gly Tyr Asp Ser Ile
705                 710                 715                 720

Arg Asn Val Thr Thr Leu Asp Ile Glu Ala Gly Arg
                725                 730
```

<210> SEQ ID NO 7
<211> LENGTH: 2226
<212> TYPE: DNA
<213> ORGANISM: Arabidopsis thaliana
<220> FEATURE:

```
<221> NAME/KEY: CDS
<222> LOCATION: (1)..(2223)
<223> OTHER INFORMATION: Wall-associated kinase 3, cDNA, complete CDS

<400> SEQUENCE: 7 atg aag ttc cag gag ggt gtg ttc ttg gtg gtt att ttc ttc ctt gca      48
Met Lys Phe Gln Glu Gly Val Phe Leu Val Val Ile Phe Phe Leu Ala
1               5                   10                  15 tat act cag ctt gtg aag ggg caa cat caa cct cgc gaa gat tgt aaa      96
Tyr Thr Gln Leu Val Lys Gly Gln His Gln Pro Arg Glu Asp Cys Lys
            20                  25                  30 ctt aaa tgt gga aac gtc aca ata gag tac cct ttt ggt att tct aca     144
Leu Lys Cys Gly Asn Val Thr Ile Glu Tyr Pro Phe Gly Ile Ser Thr
        35                  40                  45 ggt tgt tac tat ccc gga gat gat aat ttc aat ctc acc tgt gtc gtg     192
Gly Cys Tyr Tyr Pro Gly Asp Asp Asn Phe Asn Leu Thr Cys Val Val
50                  55                  60 gaa gag aag cta cta ctc ttt ggc atc att caa gtg acc aat att tct     240
Glu Glu Lys Leu Leu Leu Phe Gly Ile Ile Gln Val Thr Asn Ile Ser
65                  70                  75                  80 cac agt ggc cat gta agt gta ctg ttt gaa cga ttc tct gaa tgc tac     288
His Ser Gly His Val Ser Val Leu Phe Glu Arg Phe Ser Glu Cys Tyr
                85                  90                  95 gag cag aaa aat gag act aat gga act gcc ctc ggg tat cag ctg ggt     336
Glu Gln Lys Asn Glu Thr Asn Gly Thr Ala Leu Gly Tyr Gln Leu Gly
            100                 105                 110 agt agt ttc tct ctc tcc tcc aac aac aag ttt act tta gta gga tgt     384
Ser Ser Phe Ser Leu Ser Ser Asn Asn Lys Phe Thr Leu Val Gly Cys
        115                 120                 125 aac gct tta tca ctt ttg agc act ttt gga aag caa aac tac tca act     432
Asn Ala Leu Ser Leu Leu Ser Thr Phe Gly Lys Gln Asn Tyr Ser Thr
130                 135                 140 gga tgc ttg tca tta tgc aat tct caa cca gag gca aat gga aga tgt     480
Gly Cys Leu Ser Leu Cys Asn Ser Gln Pro Glu Ala Asn Gly Arg Cys
145                 150                 155                 160 aat ggt gta ggt tgc tgc aca aca gag gac ttc tct gtc ccg ttc gat     528
Asn Gly Val Gly Cys Cys Thr Thr Glu Asp Phe Ser Val Pro Phe Asp
                165                 170                 175 agc gat aca ttc caa ttt ggc tca gtt cgc ttg aga aac caa gtt aat     576
Ser Asp Thr Phe Gln Phe Gly Ser Val Arg Leu Arg Asn Gln Val Asn
            180                 185                 190 aat tcc tta gat cta ttt aat act tcg gta tat cag ttt aat cct tgc     624
Asn Ser Leu Asp Leu Phe Asn Thr Ser Val Tyr Gln Phe Asn Pro Cys
        195                 200                 205 acc tac gct ttt ctc gtt gaa gat ggt aag ttt aac ttc gat tct tca     672
Thr Tyr Ala Phe Leu Val Glu Asp Gly Lys Phe Asn Phe Asp Ser Ser
210                 215                 220 aaa gat ctt aag aat ctg agg aat gtc acg agg ttc cct gtg gca cta     720
Lys Asp Leu Lys Asn Leu Arg Asn Val Thr Arg Phe Pro Val Ala Leu
225                 230                 235                 240 gat tgg tct att gga aac cag aca tgt gag caa gct gga agc aca aga     768
Asp Trp Ser Ile Gly Asn Gln Thr Cys Glu Gln Ala Gly Ser Thr Arg
                245                 250                 255 ata tgc ggt aag aac agc tca tgt tac aat tct act act aga aac ggg     816
Ile Cys Gly Lys Asn Ser Ser Cys Tyr Asn Ser Thr Thr Arg Asn Gly
            260                 265                 270 tat atc tgc aaa tgt aat gaa ggt tat gat ggg aat cca tac cgt tca     864
Tyr Ile Cys Lys Cys Asn Glu Gly Tyr Asp Gly Asn Pro Tyr Arg Ser
        275                 280                 285 gag ggt tgc aaa gac atc gat gag tgt att agt gat aca cat aac tgt    912
```

|     |     |     |     |     |     |     |     |     |     |     |     |     |     |      |
|-----|-----|-----|-----|-----|-----|-----|-----|-----|-----|-----|-----|-----|-----|------|
| Glu | Gly | Cys | Lys | Asp | Ile | Asp | Glu | Cys | Ile | Ser | Asp | Thr | His | Asn Cys |
|     | 290 |     |     |     | 295 |     |     |     | 300 |     |     |     |     |      |

```
tcg gat cca aaa acc tgt aga aac agg gat gga ggc ttc gat tgt aag      960
Ser Asp Pro Lys Thr Cys Arg Asn Arg Asp Gly Gly Phe Asp Cys Lys
305                 310                 315                 320 tgt cca tct ggt tac gac tta aac tcc agt atg agc tgc acg agg ccc     1008
Cys Pro Ser Gly Tyr Asp Leu Asn Ser Ser Met Ser Cys Thr Arg Pro
                325                 330                 335 gaa tac aaa cgg act cga att ttt ctt gta atc ata atc ggc gtc ttg     1056
Glu Tyr Lys Arg Thr Arg Ile Phe Leu Val Ile Ile Ile Gly Val Leu
            340                 345                 350 gtc ctc ctg ctt gct gcg atc tgt ata caa cat gca acg aag caa agg     1104
Val Leu Leu Leu Ala Ala Ile Cys Ile Gln His Ala Thr Lys Gln Arg
        355                 360                 365 aag tat acc aag ctc cga cga caa ttc ttt gag caa aat ggt ggt ggc     1152
Lys Tyr Thr Lys Leu Arg Arg Gln Phe Phe Glu Gln Asn Gly Gly Gly
    370                 375                 380 atg ttg ata cag cga ctt tca gga gca ggg ttg tca aac att gat ttc     1200
Met Leu Ile Gln Arg Leu Ser Gly Ala Gly Leu Ser Asn Ile Asp Phe
385                 390                 395                 400 aaa atc ttt act gag gaa ggc atg aaa gag gca act aat ggc tat gat     1248
Lys Ile Phe Thr Glu Glu Gly Met Lys Glu Ala Thr Asn Gly Tyr Asp
                405                 410                 415 gag agc aga atc ttg ggc cag gga ggt caa gga aca gtc tac aaa ggg     1296
Glu Ser Arg Ile Leu Gly Gln Gly Gly Gln Gly Thr Val Tyr Lys Gly
            420                 425                 430 ata ttg ccg gac aac act atc gtt gct ata aag aaa gct cgg ctt gca     1344
Ile Leu Pro Asp Asn Thr Ile Val Ala Ile Lys Lys Ala Arg Leu Ala
        435                 440                 445 gac agt aga caa gta gat cag ttc atc cac gaa gtg ctc gtg ctt tca     1392
Asp Ser Arg Gln Val Asp Gln Phe Ile His Glu Val Leu Val Leu Ser
    450                 455                 460 caa att aac cac agg aac gtg gtc aag atc ttg ggt tgc tgt cta gag     1440
Gln Ile Asn His Arg Asn Val Val Lys Ile Leu Gly Cys Cys Leu Glu
465                 470                 475                 480 act gaa gtc ccc ttg ttg gtc tat gaa ttc att acc aat ggc acc ctt     1488
Thr Glu Val Pro Leu Leu Val Tyr Glu Phe Ile Thr Asn Gly Thr Leu
                485                 490                 495 ttc gat cac ttg cac ggt tcc att ttt gat tct tct ctt aca tgg gaa     1536
Phe Asp His Leu His Gly Ser Ile Phe Asp Ser Ser Leu Thr Trp Glu
            500                 505                 510 cac cgc ctc aga ata gcg ata gaa gtc gct gga act ctt gct tat ctt     1584
His Arg Leu Arg Ile Ala Ile Glu Val Ala Gly Thr Leu Ala Tyr Leu
        515                 520                 525 cac tcc tct gct tct att cca atc atc cat cgc gat atc aaa act gca     1632
His Ser Ser Ala Ser Ile Pro Ile Ile His Arg Asp Ile Lys Thr Ala
    530                 535                 540 aat att ctc ttg gat gaa aac tta act gca aaa gta gcc gac ttt ggc     1680
Asn Ile Leu Leu Asp Glu Asn Leu Thr Ala Lys Val Ala Asp Phe Gly
545                 550                 555                 560 gct tct aag ctt ata cca atg gat aaa gag cag ctc aca act atg gtg     1728
Ala Ser Lys Leu Ile Pro Met Asp Lys Glu Gln Leu Thr Thr Met Val
                565                 570                 575 caa ggc act cta ggc tat tta gac cca gaa tac tat acc aca ggg ctt     1776
Gln Gly Thr Leu Gly Tyr Leu Asp Pro Glu Tyr Tyr Thr Thr Gly Leu
            580                 585                 590 ctg aac gag aag agc gat gtg tat agc ttt ggg gta gtc ctc atg gaa     1824
Leu Asn Glu Lys Ser Asp Val Tyr Ser Phe Gly Val Val Leu Met Glu
        595                 600                 605
```

```
ctg ctc tca ggt caa aag gca ttg tgc ttt gaa cgg cca cag gct tca      1872
Leu Leu Ser Gly Gln Lys Ala Leu Cys Phe Glu Arg Pro Gln Ala Ser
    610             615                 620 aaa cat ttg gtg agt tac ttt gtt tct gcc acg gaa gag aat agg ttg      1920
Lys His Leu Val Ser Tyr Phe Val Ser Ala Thr Glu Glu Asn Arg Leu
625                 630                 635                 640 cat gag att att gac gac caa gtg ttg aac gag gat aat ctg aag gag      1968
His Glu Ile Ile Asp Asp Gln Val Leu Asn Glu Asp Asn Leu Lys Glu
            645                 650                 655 atc cag gaa gct gca aga att gct gca gag tgt aca agg cta atg gga      2016
Ile Gln Glu Ala Ala Arg Ile Ala Ala Glu Cys Thr Arg Leu Met Gly
                660                 665                 670 gag gaa agg cca agg atg aaa gaa gta gct gca aag cta gaa gcc ttg      2064
Glu Glu Arg Pro Arg Met Lys Glu Val Ala Ala Lys Leu Glu Ala Leu
        675                 680                 685 agg gtc gag aaa acc aaa cat aag tgg tcg gat cag tat cct gag gag      2112
Arg Val Glu Lys Thr Lys His Lys Trp Ser Asp Gln Tyr Pro Glu Glu
    690                 695                 700 aat gaa cac ttg att ggt ggt cac atc ttg tct gca caa ggc gaa acc      2160
Asn Glu His Leu Ile Gly Gly His Ile Leu Ser Ala Gln Gly Glu Thr
705                 710                 715                 720 agt agc agc att ggc tat gat agc atc aaa aat gta gca ata ttg gac      2208
Ser Ser Ser Ile Gly Tyr Asp Ser Ile Lys Asn Val Ala Ile Leu Asp
            725                 730                 735 att gaa act ggc cgc tga                                              2226
Ile Glu Thr Gly Arg
                740

<210> SEQ ID NO 8
<211> LENGTH: 741
<212> TYPE: PRT
<213> ORGANISM: Arabidopsis thaliana

<400> SEQUENCE: 8

Met Lys Phe Gln Glu Gly Val Phe Leu Val Ile Phe Phe Leu Ala
1               5                   10                  15

Tyr Thr Gln Leu Val Lys Gly Gln His Gln Pro Arg Glu Asp Cys Lys
            20                  25                  30

Leu Lys Cys Gly Asn Val Thr Ile Glu Tyr Pro Phe Gly Ile Ser Thr
        35                  40                  45

Gly Cys Tyr Tyr Pro Gly Asp Asp Asn Phe Asn Leu Thr Cys Val Val
    50                  55                  60

Glu Glu Lys Leu Leu Leu Phe Gly Ile Ile Gln Val Thr Asn Ile Ser
65                  70                  75                  80

His Ser Gly His Val Ser Val Leu Phe Glu Arg Phe Ser Glu Cys Tyr
                85                  90                  95

Glu Gln Lys Asn Glu Thr Asn Gly Thr Ala Leu Gly Tyr Gln Leu Gly
            100                 105                 110

Ser Ser Phe Ser Leu Ser Ser Asn Asn Lys Phe Thr Leu Val Gly Cys
        115                 120                 125

Asn Ala Leu Ser Leu Leu Ser Thr Phe Gly Lys Gln Asn Tyr Ser Thr
    130                 135                 140

Gly Cys Leu Ser Leu Cys Asn Ser Gln Pro Glu Ala Asn Gly Arg Cys
145                 150                 155                 160

Asn Gly Val Gly Cys Cys Thr Thr Glu Asp Phe Ser Val Pro Phe Asp
                165                 170                 175

Ser Asp Thr Phe Gln Phe Gly Ser Val Arg Leu Arg Asn Gln Val Asn
            180                 185                 190
```

```
Asn Ser Leu Asp Leu Phe Asn Thr Ser Val Tyr Gln Phe Asn Pro Cys
        195                 200                 205

Thr Tyr Ala Phe Leu Val Glu Asp Gly Lys Phe Asn Phe Asp Ser Ser
    210                 215                 220

Lys Asp Leu Lys Asn Leu Arg Asn Val Thr Arg Phe Pro Val Ala Leu
225                 230                 235                 240

Asp Trp Ser Ile Gly Asn Gln Thr Cys Glu Gln Ala Gly Ser Thr Arg
                245                 250                 255

Ile Cys Gly Lys Asn Ser Ser Cys Tyr Asn Ser Thr Thr Arg Asn Gly
                260                 265                 270

Tyr Ile Cys Lys Cys Asn Glu Gly Tyr Asp Gly Asn Pro Tyr Arg Ser
            275                 280                 285

Glu Gly Cys Lys Asp Ile Asp Glu Cys Ile Ser Asp Thr His Asn Cys
        290                 295                 300

Ser Asp Pro Lys Thr Cys Arg Asn Arg Asp Gly Gly Phe Asp Cys Lys
305                 310                 315                 320

Cys Pro Ser Gly Tyr Asp Leu Asn Ser Ser Met Ser Cys Thr Arg Pro
                325                 330                 335

Glu Tyr Lys Arg Thr Arg Ile Phe Leu Val Ile Ile Gly Val Leu
            340                 345                 350

Val Leu Leu Leu Ala Ala Ile Cys Ile Gln His Ala Thr Lys Gln Arg
        355                 360                 365

Lys Tyr Thr Lys Leu Arg Arg Gln Phe Phe Glu Gln Asn Gly Gly Gly
    370                 375                 380

Met Leu Ile Gln Arg Leu Ser Gly Ala Gly Leu Ser Asn Ile Asp Phe
385                 390                 395                 400

Lys Ile Phe Thr Glu Glu Gly Met Lys Glu Ala Thr Asn Gly Tyr Asp
                405                 410                 415

Glu Ser Arg Ile Leu Gly Gln Gly Gly Gln Gly Thr Val Tyr Lys Gly
            420                 425                 430

Ile Leu Pro Asp Asn Thr Ile Val Ala Ile Lys Lys Ala Arg Leu Ala
        435                 440                 445

Asp Ser Arg Gln Val Asp Gln Phe Ile His Glu Val Leu Val Leu Ser
    450                 455                 460

Gln Ile Asn His Arg Asn Val Val Lys Ile Leu Gly Cys Cys Leu Glu
465                 470                 475                 480

Thr Glu Val Pro Leu Leu Val Tyr Glu Phe Ile Thr Asn Gly Thr Leu
                485                 490                 495

Phe Asp His Leu His Gly Ser Ile Phe Asp Ser Ser Leu Thr Trp Glu
            500                 505                 510

His Arg Leu Arg Ile Ala Ile Glu Val Ala Gly Thr Leu Ala Tyr Leu
        515                 520                 525

His Ser Ser Ala Ser Ile Pro Ile Ile His Arg Asp Ile Lys Thr Ala
    530                 535                 540

Asn Ile Leu Leu Asp Glu Asn Leu Thr Ala Lys Val Ala Asp Phe Gly
545                 550                 555                 560

Ala Ser Lys Leu Ile Pro Met Asp Lys Glu Gln Leu Thr Thr Met Val
                565                 570                 575

Gln Gly Thr Leu Gly Tyr Leu Asp Pro Glu Tyr Tyr Thr Thr Gly Leu
            580                 585                 590

Leu Asn Glu Lys Ser Asp Val Tyr Ser Phe Gly Val Val Leu Met Glu
        595                 600                 605
```

```
Leu Leu Ser Gly Gln Lys Ala Leu Cys Phe Glu Arg Pro Gln Ala Ser
        610             615                 620
Lys His Leu Val Ser Tyr Phe Val Ser Ala Thr Glu Glu Asn Arg Leu
625                 630                 635                 640
His Glu Ile Ile Asp Asp Gln Val Leu Asn Glu Asp Asn Leu Lys Glu
                    645                 650                 655
Ile Gln Glu Ala Ala Arg Ile Ala Ala Glu Cys Thr Arg Leu Met Gly
                660                 665                 670
Glu Glu Arg Pro Arg Met Lys Glu Val Ala Ala Lys Leu Glu Ala Leu
            675                 680                 685
Arg Val Glu Lys Thr Lys His Lys Trp Ser Asp Gln Tyr Pro Glu Glu
690                 695                 700
Asn Glu His Leu Ile Gly Gly His Ile Leu Ser Ala Gln Gly Glu Thr
705                 710                 715                 720
Ser Ser Ser Ile Gly Tyr Asp Ser Ile Lys Asn Val Ala Ile Leu Asp
                725                 730                 735
Ile Glu Thr Gly Arg
            740

<210> SEQ ID NO 9
<211> LENGTH: 2202
<212> TYPE: DNA
<213> ORGANISM: Arabidopsis thaliana
<220> FEATURE:
<221> NAME/KEY: CDS
<222> LOCATION: (1)..(2199)
<223> OTHER INFORMATION: Wall-associated kinase 5, cDNA, complete CDS

<400> SEQUENCE: 9 atg aag gtg cat agt ctg ttc ttg atg gct att ttc ttc tac cta gca     48
Met Lys Val His Ser Leu Phe Leu Met Ala Ile Phe Phe Tyr Leu Ala
1               5                   10                  15 tat acg cag ctg gtc aag gcg caa cct cgc gat gat tgc caa act aga     96
Tyr Thr Gln Leu Val Lys Ala Gln Pro Arg Asp Asp Cys Gln Thr Arg
            20                  25                  30 tgt ggt gac gtc cca att gat tac cct ttt ggt att tct aca ggt tgt    144
Cys Gly Asp Val Pro Ile Asp Tyr Pro Phe Gly Ile Ser Thr Gly Cys
        35                  40                  45 tac tac ccc gga gat gat agc ttc aat att acc tgt gag gaa gat aaa    192
Tyr Tyr Pro Gly Asp Asp Ser Phe Asn Ile Thr Cys Glu Glu Asp Lys
    50                  55                  60 cca aat gtc tta agc aac att gaa gtg cta aac ttt aat cat agc ggc    240
Pro Asn Val Leu Ser Asn Ile Glu Val Leu Asn Phe Asn His Ser Gly
65                  70                  75                  80 cag cta cgc ggt ctg att cct cga tcc act gtt tgc tac gac cag caa    288
Gln Leu Arg Gly Leu Ile Pro Arg Ser Thr Val Cys Tyr Asp Gln Gln
                85                  90                  95 aca aat aat gat ttc gag tcc ctc tgg ttt cgg ttg gat aat tta tct    336
Thr Asn Asn Asp Phe Glu Ser Leu Trp Phe Arg Leu Asp Asn Leu Ser
            100                 105                 110 ttc tcc ccc aat aac aag ttt act tta gta ggc tgt aac gct tgg gca    384
Phe Ser Pro Asn Asn Lys Phe Thr Leu Val Gly Cys Asn Ala Trp Ala
        115                 120                 125 ctt cta agc act ttt gga ata caa aac tac tca act gga tgt atg tca    432
Leu Leu Ser Thr Phe Gly Ile Gln Asn Tyr Ser Thr Gly Cys Met Ser
    130                 135                 140 tta tgc gat act ccc ccg ccg cca aat agt aaa tgt aat ggt gtt ggt    480
Leu Cys Asp Thr Pro Pro Pro Pro Asn Ser Lys Cys Asn Gly Val Gly
145                 150                 155                 160
```

|  |  |
|---|---|
| tgc tgc aga aca gag gta tct atc ccc ttg gat agc cat aga att gaa<br>Cys Cys Arg Thr Glu Val Ser Ile Pro Leu Asp Ser His Arg Ile Glu<br>165                      170                    175 | 528 |
| act caa cca tct cgc ttc gaa aac atg act tcc gtg gag cac ttt aat<br>Thr Gln Pro Ser Arg Phe Glu Asn Met Thr Ser Val Glu His Phe Asn<br>180                     185                    190 | 576 |
| cct tgc agc tac gct ttt ttc gtt gaa gat ggt atg ttt aac ttc agt<br>Pro Cys Ser Tyr Ala Phe Phe Val Glu Asp Gly Met Phe Asn Phe Ser<br>        195                  200                  205 | 624 |
| tct tta gaa gat ctt aag gat ctg cga aat gtc acg agg ttc cct gtg<br>Ser Leu Glu Asp Leu Lys Asp Leu Arg Asn Val Thr Arg Phe Pro Val<br>210                     215                    220 | 672 |
| tta cta gat tgg tct att gga aac cag aca tgt gag caa gtt gta ggt<br>Leu Leu Asp Trp Ser Ile Gly Asn Gln Thr Cys Glu Gln Val Val Gly<br>225                   230                   235                  240 | 720 |
| aga aac ata tgt ggt ggg aac agc aca tgt ttt gat tct act cgt gga<br>Arg Asn Ile Cys Gly Gly Asn Ser Thr Cys Phe Asp Ser Thr Arg Gly<br>                245                  250                  255 | 768 |
| aag ggt tat aac tgc aag tgt tta caa ggt ttt gat ggg aat cca tac<br>Lys Gly Tyr Asn Cys Lys Cys Leu Gln Gly Phe Asp Gly Asn Pro Tyr<br>260                     265                    270 | 816 |
| ctt tcg gac ggt tgc caa gac atc aat gag tgt act acc cgt ata cat<br>Leu Ser Asp Gly Cys Gln Asp Ile Asn Glu Cys Thr Thr Arg Ile His<br>        275                  280                  285 | 864 |
| aac tgt tcg gat acc agc aca tgt gaa aac aca ctt gga agc ttc cat<br>Asn Cys Ser Asp Thr Ser Thr Cys Glu Asn Thr Leu Gly Ser Phe His<br>290                     295                    300 | 912 |
| tgt cag tgc cca tct ggt tct gat tta aat acc act act atg agc tgc<br>Cys Gln Cys Pro Ser Gly Ser Asp Leu Asn Thr Thr Thr Met Ser Cys<br>305                   310                   315                  320 | 960 |
| att gac aca cct aaa gaa gag cct aag tac tta gga tgg act act gtt<br>Ile Asp Thr Pro Lys Glu Glu Pro Lys Tyr Leu Gly Trp Thr Thr Val<br>                325                  330                  335 | 1008 |
| ctt ctt gga acc acc atc gga ttc tta atc atc ttg ctt acc att agc<br>Leu Leu Gly Thr Thr Ile Gly Phe Leu Ile Ile Leu Leu Thr Ile Ser<br>                340                  345                  350 | 1056 |
| tat ata caa caa aaa atg agg cac cga aaa aac acc gag ctg cga caa<br>Tyr Ile Gln Gln Lys Met Arg His Arg Lys Asn Thr Glu Leu Arg Gln<br>355                     360                    365 | 1104 |
| caa ttc ttc gag caa aat ggt ggt ggc atg ttg ata cag cga ctc tca<br>Gln Phe Phe Glu Gln Asn Gly Gly Gly Met Leu Ile Gln Arg Leu Ser<br>370                   375                   380 | 1152 |
| gga gca ggg cca tca aat gtg gat gtc aaa atc ttt act gaa gaa ggc<br>Gly Ala Gly Pro Ser Asn Val Asp Val Lys Ile Phe Thr Glu Glu Gly<br>385                   390                   395                  400 | 1200 |
| atg aag gaa gca act gat ggt tat aat gag agc aga atc cta ggc cag<br>Met Lys Glu Ala Thr Asp Gly Tyr Asn Glu Ser Arg Ile Leu Gly Gln<br>                405                  410                  415 | 1248 |
| gga gga caa gga aca gtc tac aaa ggg ata ttg caa gat aac tcc att<br>Gly Gly Gln Gly Thr Val Tyr Lys Gly Ile Leu Gln Asp Asn Ser Ile<br>        420                  425                  430 | 1296 |
| gtt gct ata aag aaa gct cga ctt gga gac cgt agc caa gta gag cag<br>Val Ala Ile Lys Lys Ala Arg Leu Gly Asp Arg Ser Gln Val Glu Gln<br>435                     440                    445 | 1344 |
| ttc atc aac gaa gtg cta gtg ctt tca caa ata aac cac agg aac gtg<br>Phe Ile Asn Glu Val Leu Val Leu Ser Gln Ile Asn His Arg Asn Val<br>450                     455                    460 | 1392 |
| gtc aaa ctc ttg ggc tgt tgt cta gag act gaa gtt ccc ttg ttg gtc<br>Val Lys Leu Leu Gly Cys Cys Leu Glu Thr Glu Val Pro Leu Leu Val<br>465                     470                   475                  480 | 1440 |

```
tat gag ttc att tcc agt ggc act ctt ttt gat cac ttg cac ggt tct      1488
Tyr Glu Phe Ile Ser Ser Gly Thr Leu Phe Asp His Leu His Gly Ser
                485                 490                 495 atg ttt gat tct tcg ctt aca tgg gaa cac cgt ctg agg ata gcc ata      1536
Met Phe Asp Ser Ser Leu Thr Trp Glu His Arg Leu Arg Ile Ala Ile
            500                 505                 510 gaa gtt gct gga act ctt gca tat ctt cac tcc tat gct tct att cca      1584
Glu Val Ala Gly Thr Leu Ala Tyr Leu His Ser Tyr Ala Ser Ile Pro
        515                 520                 525 atc atc cac cga gat gtc aag act gct aac att ctc ctc gat gaa aac      1632
Ile Ile His Arg Asp Val Lys Thr Ala Asn Ile Leu Leu Asp Glu Asn
    530                 535                 540 tta act gca aaa gta gct gat ttt ggt gca tca agg ctg ata ccg atg      1680
Leu Thr Ala Lys Val Ala Asp Phe Gly Ala Ser Arg Leu Ile Pro Met
545                 550                 555                 560 gac caa gag cag ctc aca act atg gtt caa gga act ctt ggc tat tta      1728
Asp Gln Glu Gln Leu Thr Thr Met Val Gln Gly Thr Leu Gly Tyr Leu
                565                 570                 575 gac cct gaa tac tac aat aca ggg ctt ctg aac gaa aag agc gat gtt      1776
Asp Pro Glu Tyr Tyr Asn Thr Gly Leu Leu Asn Glu Lys Ser Asp Val
            580                 585                 590 tat agc ttt ggg gta gtc ctc atg gaa ctg ctc tca ggt gaa aag gca      1824
Tyr Ser Phe Gly Val Val Leu Met Glu Leu Leu Ser Gly Glu Lys Ala
        595                 600                 605 tta tgc ttt gaa cgg cca caa agc tca aaa cat cta gtg agt tac ttt      1872
Leu Cys Phe Glu Arg Pro Gln Ser Ser Lys His Leu Val Ser Tyr Phe
    610                 615                 620 gtt tct gcc atg aaa gaa aat agg ttg cat gag att att gac ggt caa      1920
Val Ser Ala Met Lys Glu Asn Arg Leu His Glu Ile Ile Asp Gly Gln
625                 630                 635                 640 gtt atg aac gag tat aat cag agg gag atc cag gaa tct gca aga att      1968
Val Met Asn Glu Tyr Asn Gln Arg Glu Ile Gln Glu Ser Ala Arg Ile
                645                 650                 655 gct gtt gag tgt aca aga att atg gga gag gaa agg cca agt atg aaa      2016
Ala Val Glu Cys Thr Arg Ile Met Gly Glu Glu Arg Pro Ser Met Lys
            660                 665                 670 gaa gta gct gca gag tta gag gcc ttg aga gtc aaa aca acc aaa cat      2064
Glu Val Ala Ala Glu Leu Glu Ala Leu Arg Val Lys Thr Thr Lys His
        675                 680                 685 cag tgg tca gat caa tat ccc aag gag gtt gag cat ttg ctt ggt gtt      2112
Gln Trp Ser Asp Gln Tyr Pro Lys Glu Val Glu His Leu Leu Gly Val
    690                 695                 700 caa atc tta tcg acg caa ggt gat acc agt agc att ggc tat gac agc      2160
Gln Ile Leu Ser Thr Gln Gly Asp Thr Ser Ser Ile Gly Tyr Asp Ser
705                 710                 715                 720 atc cag aat gta aca agg ttg gac att gaa act ggc cgc tga              2202
Ile Gln Asn Val Thr Arg Leu Asp Ile Glu Thr Gly Arg
                725                 730

<210> SEQ ID NO 10
<211> LENGTH: 733
<212> TYPE: PRT
<213> ORGANISM: Arabidopsis thaliana

<400> SEQUENCE: 10

Met Lys Val His Ser Leu Phe Leu Met Ala Ile Phe Phe Tyr Leu Ala
1               5                   10                  15

Tyr Thr Gln Leu Val Lys Ala Gln Pro Arg Asp Asp Cys Gln Thr Arg
            20                  25                  30
```

-continued

```
Cys Gly Asp Val Pro Ile Asp Tyr Pro Phe Gly Ile Ser Thr Gly Cys
         35                  40                  45

Tyr Tyr Pro Gly Asp Asp Ser Phe Asn Ile Thr Cys Glu Glu Asp Lys
 50                  55                  60

Pro Asn Val Leu Ser Asn Ile Glu Val Leu Asn Phe Asn His Ser Gly
65                  70                  75                  80

Gln Leu Arg Gly Leu Ile Pro Arg Ser Thr Val Cys Tyr Asp Gln Gln
                 85                  90                  95

Thr Asn Asn Asp Phe Glu Ser Leu Trp Phe Arg Leu Asn Leu Asn Leu Ser
             100                 105                 110

Phe Ser Pro Asn Asn Lys Phe Thr Leu Val Gly Cys Asn Ala Trp Ala
             115                 120                 125

Leu Leu Ser Thr Phe Gly Ile Gln Asn Tyr Ser Thr Gly Cys Met Ser
    130                 135                 140

Leu Cys Asp Thr Pro Pro Pro Asn Ser Lys Cys Asn Gly Val Gly
145                 150                 155                 160

Cys Cys Arg Thr Glu Val Ser Ile Pro Leu Asp Ser His Arg Ile Glu
                165                 170                 175

Thr Gln Pro Ser Arg Phe Glu Asn Met Thr Ser Val Glu His Phe Asn
            180                 185                 190

Pro Cys Ser Tyr Ala Phe Phe Val Glu Asp Gly Met Phe Asn Phe Ser
            195                 200                 205

Ser Leu Glu Asp Leu Lys Asp Leu Arg Asn Val Thr Arg Phe Pro Val
    210                 215                 220

Leu Leu Asp Trp Ser Ile Gly Asn Gln Thr Cys Glu Gln Val Val Gly
225                 230                 235                 240

Arg Asn Ile Cys Gly Gly Asn Ser Thr Cys Phe Asp Ser Thr Arg Gly
                245                 250                 255

Lys Gly Tyr Asn Cys Lys Cys Leu Gln Gly Phe Asp Gly Asn Pro Tyr
            260                 265                 270

Leu Ser Asp Gly Cys Gln Asp Ile Asn Glu Cys Thr Thr Arg Ile His
    275                 280                 285

Asn Cys Ser Asp Thr Ser Thr Cys Glu Asn Thr Leu Gly Ser Phe His
    290                 295                 300

Cys Gln Cys Pro Ser Gly Ser Asp Leu Asn Thr Thr Met Ser Cys
305                 310                 315                 320

Ile Asp Thr Pro Lys Glu Glu Pro Lys Tyr Leu Gly Trp Thr Thr Val
                325                 330                 335

Leu Leu Gly Thr Thr Ile Gly Phe Leu Ile Ile Leu Thr Ile Ser
            340                 345                 350

Tyr Ile Gln Gln Lys Met Arg His Arg Lys Asn Thr Glu Leu Arg Gln
    355                 360                 365

Gln Phe Phe Glu Gln Asn Gly Gly Met Leu Ile Gln Arg Leu Ser
    370                 375                 380

Gly Ala Gly Pro Ser Asn Val Asp Val Lys Ile Phe Thr Glu Glu Gly
385                 390                 395                 400

Met Lys Glu Ala Thr Asp Gly Tyr Asn Glu Ser Arg Ile Leu Gly Gln
                405                 410                 415

Gly Gly Gln Gly Thr Val Tyr Lys Gly Ile Leu Gln Asp Asn Ser Ile
            420                 425                 430

Val Ala Ile Lys Lys Ala Arg Leu Gly Asp Arg Ser Gln Val Glu Gln
            435                 440                 445

Phe Ile Asn Glu Val Leu Val Leu Ser Gln Ile Asn His Arg Asn Val
```

```
        450                 455                 460
Val Lys Leu Leu Gly Cys Cys Leu Glu Thr Glu Val Pro Leu Leu Val
465                 470                 475                 480

Tyr Glu Phe Ile Ser Ser Gly Thr Leu Phe Asp His Leu His Gly Ser
                485                 490                 495

Met Phe Asp Ser Ser Leu Thr Trp Glu His Arg Leu Arg Ile Ala Ile
                500                 505                 510

Glu Val Ala Gly Thr Leu Ala Tyr Leu His Ser Tyr Ala Ser Ile Pro
            515                 520                 525

Ile Ile His Arg Asp Val Lys Thr Ala Asn Ile Leu Leu Asp Glu Asn
        530                 535                 540

Leu Thr Ala Lys Val Ala Asp Phe Gly Ala Ser Arg Leu Ile Pro Met
545                 550                 555                 560

Asp Gln Glu Gln Leu Thr Thr Met Val Gln Gly Thr Leu Gly Tyr Leu
                565                 570                 575

Asp Pro Glu Tyr Tyr Asn Thr Gly Leu Leu Asn Glu Lys Ser Asp Val
            580                 585                 590

Tyr Ser Phe Gly Val Val Leu Met Glu Leu Leu Ser Gly Glu Lys Ala
        595                 600                 605

Leu Cys Phe Glu Arg Pro Gln Ser Ser Lys His Leu Val Ser Tyr Phe
610                 615                 620

Val Ser Ala Met Lys Glu Asn Arg Leu His Glu Ile Ile Asp Gly Gln
625                 630                 635                 640

Val Met Asn Glu Tyr Asn Gln Arg Glu Ile Gln Glu Ser Ala Arg Ile
                645                 650                 655

Ala Val Glu Cys Thr Arg Ile Met Gly Glu Arg Pro Ser Met Lys
            660                 665                 670

Glu Val Ala Ala Glu Leu Glu Ala Leu Arg Val Lys Thr Thr Lys His
        675                 680                 685

Gln Trp Ser Asp Gln Tyr Pro Lys Glu Val His Leu Leu Gly Val
    690                 695                 700

Gln Ile Leu Ser Thr Gln Gly Asp Thr Ser Ser Ile Gly Tyr Asp Ser
705                 710                 715                 720

Ile Gln Asn Val Thr Arg Leu Asp Ile Glu Thr Gly Arg
                725                 730
```

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      WAK_NDE primer

<400> SEQUENCE: 11
catatgaaag tgcagcgtct gtt                                         23

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      WAK_XBA primer

<400> SEQUENCE: 12
tctagatcag cggcctgctt caa                                         23

NUCLEIC ACID CONSTRUCTS METHODS FOR ALTERING PLANT FIBER LENGTH AND/OR PLANT HEIGHT

CROSS-REFERENCE TO RELATED APPLICATION

This application is the National Stage of International Application No. PCT/BR07/00357, filed Dec. 20, 2007, which claims the benefit under 35 U.S.C. §119(e) of U.S. Provisional Application No. 60/871,048, filed Dec. 20, 2006, the disclosure of which is incorporated by reference in its entirety.

FIELD OF THE INVENTION

The present invention relates to the fields of molecular biology and alteration of gene expression in transformed plants. More specifically, this invention relates to the modification of fiber length and/or plant height in plants of industrial interest by regulation of expression of genes encoding wall-associated kinases (WAKs).

BACKGROUND OF THE INVENTION

The increasing demand for wood products and wood derived products constitutes a problem of global proportion. It is estimated that the maximum sustainable rate of harvesting from the world's forests has already been reached. Thus, there is an imminent need for more woody plants, as well as a need for developing methods for increasing the agronomic properties of forestry plants, such as enhanced plant height, enhanced biomass production, and longer xylem fiber length. For example, fiber uniformity and strength are common requirements for most industrial uses. In pulp manufacture, strength characteristics are determined in part by fiber length. Long fibers are ideal for strong paper production, pulp yield increase and decrease in alkali consumption, due to their strength and bonding properties.

As an illustrative example of the importance of woody plants, one can mention *Eucalyptus* trees, which represent the largest sources of fibers used globally in the paper industry. Bamber, 1985, *Appita* 38: 210-216). There are an estimated ten to fifteen million hectares of land planted with *Eucalyptus*. Verhaegen and Plomion, 1996, *Genome* 39: 1051-1061. The major advantage of the *Eucalyptus* tree is its very high growth rate and ability to grow in a wide range of conditions, both tropical and temperate. The *Eucalyptus* fibers have one disadvantage, however, compared to fibers from other sources, such as pine, which is their significantly shorter length. Thus, papers that are made from *Eucalyptus* pulp are often weak and usually require reinforcement with longer fibers from other sources increasing the production costs.

Fiber length is controlled by endogenous regulation of cell elongation, a process which results from the interaction between internal turgor pressure and the mechanical strength of the cell wall, but its mechanism and genes involved have not been yet totally discerned.

Xylem fiber cells develop from already much-elongated fusiform initials located within the vascular cambium. They increase in diameter by extension of their radial walls, and, in addition, developing fiber cells elongate by intrusive tip growth, which results in up to a severalfold increase in cell length. Gray-Mitsumune et al., 2004, *Plant Physiol.* 135: 1552-1564.

In tip-growing cells, expansion occurs over a small area of the cell surface, which results in tubular, elongated cells. For example, poplar fibers elongate intrusively in the radial-expansion zone in the xylem, reaching 150% of their initial cell length at the average when fully differentiated. Hussey et al., 2006, *Annu. Rev. Plant Biol.* 57: 109-125; Mellerowicz et al., 2001, *Plant Mol. Biol.* 47: 239-274.

The rapid expansion of fiber cells may be achieved by concerted action of pushing against the cell wall exerted by turgor and loosening of the cell wall. In cotton fibers, the phase of cell elongation follows a significant rise of turgor, resulted from the observed accumulation of malate, sugars, and $K^+$, the major osmoticum, hence the influx of water and the generation of high turgor in the fiber cells. Ruan et al., 2004, *Plant Physiol.* 136: 4104-4113.

Vacuolar invertases can play an important role in turgor maintenance and cell wall expansion. Recent work in *Arabidopsis thaliana* has shown that a wall-associated kinase (WAK) can regulate a vacuolar invertase thus establishing a cross-compartmental link between WAK and vacuolar invertase(s). Kohorn et al., 2006, *Plant J.* 46: 307-316.

In *Arabidopsis* WAKs are encoded by five tightly linked and highly similar genes, and are expressed in leaves, meristems, and cells undergoing expansion. Wagner and Kohorn, 2001, *Plant Cell* 13: 303-318.

Mutant seedlings of *Arabidopsis thaliana* presenting a T-DNA insertion in the WAK2 gene were significantly shorter than wild-type plants, with the roots more affected than the hypocotyls. Kohorn et al., 2006, *Plant J.* 46: 307-316.

These mutant plants showed a reduced vacuolar invertase activity by 62%, and the authors proposed that WAK2 regulates the transcription of vacuolar invertase as one constituent of a mechanism modulating solute concentrations and turgor regulation, thus providing a possible mechanism for WAK to regulate cell expansion.

The expression of an inducible antisense WAK2 in *Arabidopsis* led to a 50% reduction in WAK protein levels, with a subsequent loss of cell elongation, and hence dwarf plants. Similar results have been reported when an antisense WAK4 gene was used to reduce total WAK protein levels. Wagner and Kohorn, 2001, *Plant Cell* 13: 303-318; Lally et al., 2001, *Plant Cell* 13: 1317-1331.

It is also known that the wall-associated kinases contain extracellular domains that can be linked to pectin molecules of the cell wall, span the plasma membrane and have a cytoplasmic serine/threonine kinase domain. He et al., 1999, *Plant Mol. Biol.* 39: 1189-1196.

When fibers undergo significant elongation at both ends (intrusive tip growth), the properties of the middle lamella limit this type of cell growth. Middle lamellae of developing wood cells are rich in pectins, and intrusive tip growth requires the dissolution of the middle lamella. See Berthold et al., WO 2006/068603.

By their pectin attachment, it is possible that WAKs may sense a change in the cell wall environment, thus providing a molecular mechanism linking cell wall sensing to regulation of solute metabolism, which in turn is known to be involved in turgor maintenance and cell expansion in growing cells. Such information could be invaluable to adjustment of cell expansion or turgor. Huang et al., 2007, *Functional Plant Biology*, 34: 499-507.

Fiber characteristics are controlled by a complex set of genetic factors and are not easily amenable to classical breeding methods. Through traditional forest tree breeding it is possible to achieve some modification of fiber characteristics. For example, interspecific triploid hybrids of poplar have been developed which have longer fibers than the parental species. Aziz et al., 1996, Wood and pulp properties of aspen and its hybrids. *TAPPI Proc. Pulping Conference*. p. 437-443.

Yet, considering the disadvantage of traditional forest tree breeding, such as the slow progress due to their long generation periods and the difficulty of producing a plant with a desirable trait, the developments in gene technology can reduce significantly the time required to produce a new variety of plant and allow closer targeting of traits considered desirable by the forest and pulp industries in specific trees species.

SUMMARY OF THE INVENTION

In one aspect, the invention provides a nucleic acid construct comprising a WAK polynucleotide sequence operably linked to a xylem-preferred promoter that causes overexpression of said WAK polynucleotide sequence. In an embodiment, the xylem-preferred promoter is selected from the group consisting of TUB gene promoter, SuSy gene promoter, COMT gene promoter and C4H gene promoter. In another embodiment, a transgenic plant comprises the nucleic acid construct and the plant has an increase in fiber length and/or height compared to a non-transgenic plant of the same species. In further embodiments the plant is a dicotyledon, monocotyledon, gymnosperm, or hardwood tree. The invention further contemplates the progeny of the transgenic plant, as well as wood pulp and wood fiber produced from the transgenic plant.

In another aspect, the invention provides a method for increasing fiber length and/or plant height, comprising: (a) introducing into a plant cell a nucleic acid construct comprising a WAK polynucleotide sequence operably linked to a xylem-preferred promoter that causes overexpression of said WAK polynucleotide sequence; (b) culturing said plant cell under conditions that promote growth of a plant; and (c) selecting a transgenic plant that has increased fiber length and/or plant height compared to a non-transgenic plant of the same species.

DETAILED DESCRIPTION OF THE INVENTION

Figure 1:
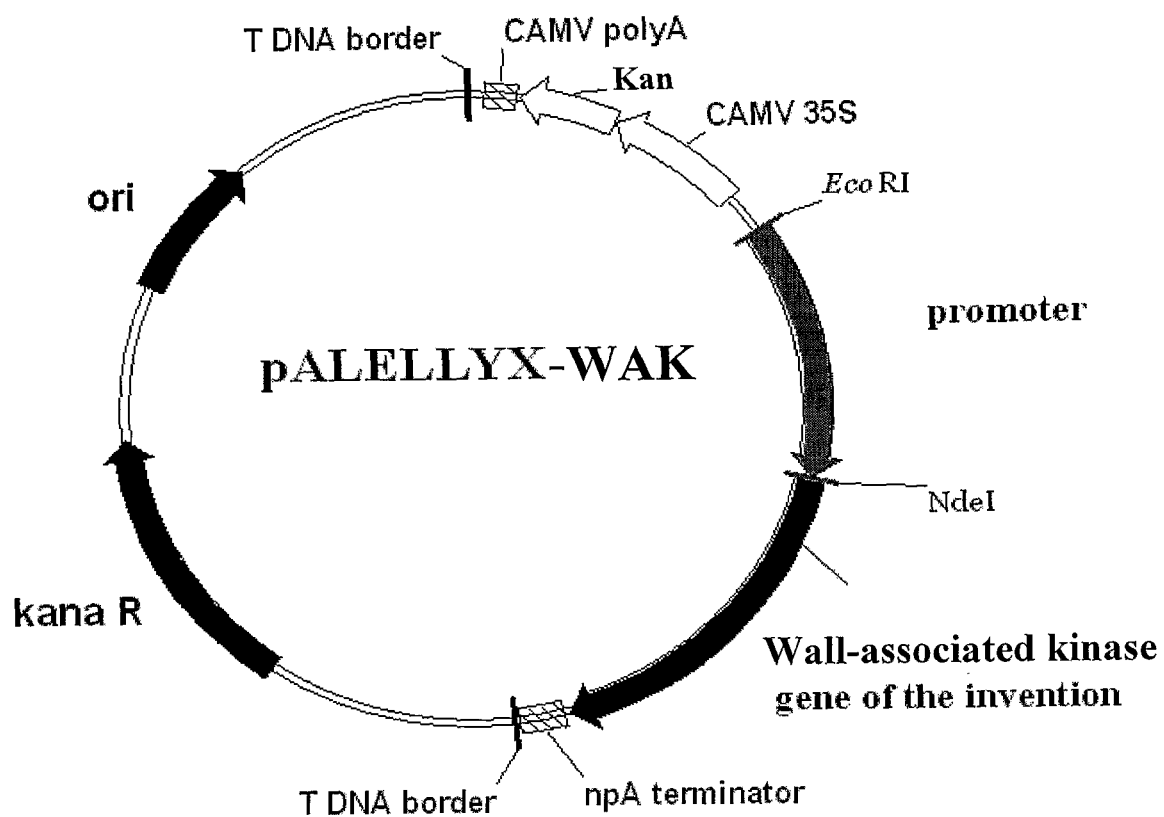
FIG. 1 schematically illustrates the plant expression plasmidial vector pALELLYX-WAK of the invention comprising a cambium/xylem preferred promoter driving the expression of a wall-associated kinase nucleotide sequence of the invention.

The present invention relates to processes for genetic manipulation of fiber length in plants and/or an increase in plant height.

The plant cell wall is a strong fibrillar network that gives each cell its stable shape. To enlarge, cells selectively loose this network, enabling it to yield to the expansive forces generated by cell turgor pressure. As a cell expands, there is increased need for a compensatory adjustment in turgor, which is dependent on cell solute metabolism.

A wall-associated kinase (WAK) may sense cell wall expansion by its attachment to pectin, thereby providing a mechanism for transducing these signals to systems regulating solute changes, as outlined above. The previous work on WAKs, however, did not presage that the overexpression of a WAK gene in plant, in a tissue-specific manner, results in significant changes in fiber length, as well as significant changes in plant height. The result opens the way to modifying traits that are extremely important for the plant fiber, forest, pulp, and paper industries.

According to an aspect of the present invention, therefore, a method is provided for modifying the fiber length in plant tissues, such as fiber cells of woody angiosperm xylem, tracheid cells of gymnosperm xylem, and fiber cells of cotton seeds, by controlling the activity of a wall-associated kinase. Pursuant to this aspect of the invention, plant cells or whole plants are genetically engineered with a wall-associated kinase coding sequence, which, when expressed in xylary fiber cells of angiosperms, xylary tracheids of gymnosperms, or fiber cells of cotton seeds, causes an increase in cell length.

All technical terms used herein are terms commonly used in biochemistry, molecular biology and agriculture, and can be understood by one of ordinary skill in the art to which this invention belongs. Those technical terms can be found in: MOLECULAR CLONING: A LABORATORY MANUAL, 3rd ed., vol. 1-3, ed. Sambrook and Russel, Cold Spring Harbor Laboratory Press, Cold Spring Harbor, N.Y., 2001; CURRENT PROTOCOLS IN MOLECULAR BIOLOGY, ed. Ausubel et al., Greene Publishing Associates and Wiley-Interscience, New York, 1988 (with periodic updates); SHORT PROTOCOLS IN MOLECULAR BIOLOGY: A COMPENDIUM OF METHODS FROM CURRENT PROTOCOLS IN MOLECULAR BIOLOGY, $5^{th}$ ed., vol. 1-2, ed. Ausubel et al., John Wiley & Sons, Inc., 2002; GENOME ANALYSIS: A LABORATORY MANUAL, vol. 1-2, ed. Green et al., Cold Spring Harbor Laboratory Press, Cold Spring Harbor, N.Y., 1997. Methodology involving plant biology techniques is described herein and is described in detail in treatises such as METHODS IN PLANT MOLECULAR BIOLOGY: A LABORATORY COURSE MANUAL, ed. Maliga et al., Cold Spring Harbor Laboratory Press, Cold Spring Harbor, N.Y., 1995. Various techniques using PCR are described, e.g., in Innis et al., PCR PROTOCOLS: A GUIDE TO METHODS AND APPLICATIONS, Academic Press, San Diego, 1990 and in Dieffenbach and Dveksler, PCR PRIMER: A LABORATORY MANUAL, $2^{nd}$ ed., Cold Spring Harbor Laboratory Press, Cold Spring Harbor, N.Y., 2003. PCR-primer pairs can be derived from known sequences by known techniques such as using computer programs intended for that purpose, e.g., Primer, Version 0.5, 1991, Whitehead Institute for Biomedical Research, Cambridge, Mass. Methods for chemical synthesis of nucleic acids are discussed, for example, in Beaucage and Caruthers, 1981, Tetra. Letts. 22: 1859-1862, and Matteucci and Caruthers, 1981, J. Am. Chem. Soc. 103: 3185.

Restriction enzyme digestions, phosphorylations, ligations and transformations were done as described in Sambrook et al., MOLECULAR CLONING: A LABORATORY MANUAL, $2^{nd}$ ed. (1989), Cold Spring Harbor Laboratory Press. All reagents and materials used for the growth and maintenance of bacterial cells were obtained from Aldrich Chemicals (Milwaukee, Wis.), DIFCO Laboratories (Detroit, Mich.), Invitrogen (Gaithersburg, Md.), or Sigma Chemical Company (St. Louis, Mo.) unless otherwise specified.

The terms "encoding" and "coding" refer to the process by which a gene, through the mechanisms of transcription and translation, provides information to a cell from which a series of amino acids can be assembled into a specific amino acid sequence to produce an active enzyme. Because of the degeneracy of the genetic code, certain base changes in DNA sequence do not change the amino acid sequence of a protein. It is therefore understood that modifications in the DNA sequence encoding wall-associated kinase which do not substantially affect the functional properties of the protein are contemplated.

In this description, "expression" denotes the production of the protein product encoded by a gene. Alternatively or additionally, "expression" denotes the combination of intracellular processes, including transcription and translation, undergone by a coding DNA molecule such as a structural gene to produce a polypeptide. "Overexpression" refers to the expression of a particular gene sequence in which the production of mRNA or polypeptide in a transgenic organism exceeds the levels of production in non-transgenic organism.

The term "heterologous nucleic acid" refers to a nucleic acid, DNA or RNA, which has been introduced into a cell (or the cell's ancestor) through the efforts of humans. Such exogenous nucleic acid may be a copy of a sequence which is naturally found in the cell into which it was introduced, or fragments thereof.

In contrast, the term "endogenous nucleic acid" refers to a nucleic acid, gene, polynucleotide, DNA, RNA, mRNA, or cDNA molecule that is present in a plant or organism that is to be genetically engineered. An endogenous sequence is "native" to, i.e., indigenous to, the plant or organism that is to be genetically engineered.

The term "homologous sequences" refers to polynucleotide or polypeptide sequences that are similar due to common ancestry and sequence conservation.

The term "functional homolog" refers to a polynucleotide or polypeptide sequences that are similar due to common ancestry and sequence conservation and have identical or similar function at the catalytic, cellular, or organismal levels.

Wall-Associated Kinase Sequences

In this description, the term "wall-associated kinase polynucleotide sequence" denotes any nucleic acid, gene, polynucleotide, DNA, RNA, mRNA, or cDNA molecule that encodes a wall-associated kinase polypeptide whose overexpression alters fiber length and/or plant height. The DNA or RNA may be double-stranded or single-stranded. Single-stranded DNA may be the coding strand, also known as the sense strand, or it may be the non-coding strand, also called the anti-sense strand. Illustrative of this category are polynucleotide molecules that comprise SEQ ID NOs: 1, 3, 5, 7 and 9, identified from *Arabidopsis thaliana* and that can be employed to enhance fiber length and/or plant height.

A wall-associated kinase polynucleotide sequence suitable for the present invention may be identified from a myriad of organisms characterized by the presence of a WAK gene. Although the aforementioned nucleotide sequences are disclosed herein, they are not to be taken as limitations on the present invention. Thus, a WAK sequence can be identified and functionally annotated by sequence comparison. The skilled person can readily identify a functionally related WAK sequence in a suitable database, such as GenBank, using publicly available sequence-analysis programs and parameters. Alternatively, screening cDNA libraries or genomic libraries employing suitable hybridization probes or primers based on DNA or protein sequences disclosed herein should lead to the identification of functionally related WAK sequences (functional homolog). It is appreciated in the field as well that sequences with reduced levels of identity also can be isolated with the aid of degenerate oligonucleotides and PCR-based methodology. While the polynucleotides of the inventions are isolated from *Arabidopsis thaliana*, functional homologs from other plants can be employed to produce plants with enhanced fiber length and/or plant height. Examples of plant species from which WAK genes may be isolated include dicotyledons, such as Cucurbitaceae, Solanaceae, Brassicaceae, Papilionaceae such as alfalfa and *Vigna unguiculata*, Malvaceae, Asteraceae, Malpighiaceae such as *Populus*, Myrtaceae such as *Eucalyptus*, and monocotyledons, such as gramineae, including rice, wheat, sugarcane, barley, and corn.

In this description, the terms "wall-associated kinase polynucleotide sequence," "WAK polynucleotide sequence" and "WAK DNA sequence" also refer to any nucleic acid molecule with a nucleotide sequence capable of hybridizing under stringent conditions with any of the sequences disclosed herein, and coding for a polypeptide with WAK activity equivalent to the proteins having amino acid sequences disclosed herein under SEQ ID NOs: 2, 4, 6, 8, or 10. The terms also include sequences which cross-hybridize with SEQ ID NO: 1, SEQ ID NO: 3, SEQ ID NO: 5, SEQ ID NO: 7 or SEQ ID NO: 9, preferably having at least 65% homology or identity with one or more of SEQ ID NO: 1, 3, 5, 7 or 9. The nucleotide sequences of the invention may encode a protein which is homologous to the predicted gene product disclosed herein under any of SEQ ID NOs: 2, 4, 6, 8, or 10. Further, the nucleotide sequences of the invention include those sequences that encode a WAK polypeptide having an amino acid sequence which has at least 55%, preferably at least 60%, more preferably at least 70%, more preferably at least 80%, more preferably at least 90% and most preferably at least 95% sequence identity to an amino acid sequence disclosed herein under any of SEQ ID NOs: 2, 4, 6, 8 and 10. The degeneracy of the genetic code enables major variations in the nucleotide sequence of a polynucleotide while maintaining the amino acid sequence of the encoded protein.

The phrase "stringent conditions" here connotes parameters with which the art is familiar. Single-stranded polynucleotides hybridize when they associate based on a variety of well-characterized physicochemical forces, such as hydrogen bonding, solvent exclusion, and base stacking. The stringency of a hybridization reflects the degree of sequence identity of the nucleic acids involved, such that the higher the stringency, the more similar are the two polynucleotide strands. Stringency is influenced by a variety of factors, including temperature, salt concentration and composition, organic and non-organic additives, solvents, etc. present in both the hybridization and wash solutions and incubations (and number). One with ordinary skill in the art can readily select such conditions by varying the temperature during the hybridization reaction and washing process, the salt concentration during the hybridization reaction and washing process, and so forth.

For hybridization of complementary nucleic acids which have more than 100 complementary residues, on a filter in a Southern or Northern blot, "stringent" hybridization conditions are exemplified by a temperature that is about 5° C. to 20° C. lower than the thermal melting point (Tm) for the specific sequence, at a defined ionic strength and pH. The Tm is the temperature, under defined ionic strength and pH, at which 50% of the target sequence hybridizes to a perfectly matched probe. Nucleic acid molecules that hybridize under stringent conditions typically will hybridize to a probe based on either the entire cDNA or selected portions. More preferably, "stringent conditions" here refers to parameters with which the art is familiar, such as hybridization in 3.5×SSC, 1×Denhardt's solution, 25 mM sodium phosphate buffer (pH 7.0), 0.5% SDS, and 2 mM EDTA for 18 hours at 65° C., followed by four washes of the filter, at 65° C. for 20 minutes, in 2×SSC and 0.1% SDS, and a final wash for up to 20 minutes in 0.5×SSC and 0.1% SDS or 0.3×SSC and 0.1% SDS for greater stringency, and 0.1×SSC and 0.1% SDS for even greater stringency. Other conditions may be substituted, as long as the degree of stringency is equal to that provided herein, using a 0.5×SSC final wash. For identification of less closely related homologues washes can be performed at a lower temperature, e.g., 50° C. In general, stringency is increased by raising the wash temperature and/or decreasing the concentration of SSC.

Additionally, the category of suitable wall-associated kinase sequences includes a nucleic acid molecule comprised of a variant of SEQ ID NOs: 1 or 3 or 5 or 7 or 9 with one or more bases deleted, substituted, inserted, or added, which variant codes for a polypeptide when overexpressed results in alteration in fiber length and/or plant height. The "base sequences with one or more bases deleted, substituted, inserted, or added" referred to here are widely known by those having ordinary skill in the art to retain physiological activity even when the amino acid sequence of a protein generally having that physiological activity has one or more amino acids substituted, deleted, inserted, or added. For example, the poly A tail or 5' or 3' end nontranslation regions may be deleted, and bases may be deleted to the extent that amino acids are deleted. Bases may also be substituted, as long as no frame shift results. Bases also may be "added" to the extent that amino acids are added. It is essential, however, that any such modification does not result in the loss of physiological activity. A modified DNA in this context can be obtained by modifying the DNA base sequences of the invention so that amino acids at specific sites are substituted, deleted, inserted, or added by site-specific mutagenesis, for example. Zoller & Smith, 1982, *Nucleic Acid Res.* 10: 6487-6500. Accordingly, the term "variant" is a nucleotide or amino acid sequence that deviates from the standard, or given, nucleotide or amino acid sequence of a particular gene or protein. The variant may have "conservative" changes, wherein a substituted amino acid has similar structural or chemical properties, e.g., replacement of leucine with isoleucine. A variant may have "nonconservative" changes, e.g., replacement of a glycine with a tryptophan. Analogous minor variations may also include amino acid deletions or insertions, or both. Guidance in determining which amino acid residues may be substituted, inserted, or deleted may be found using computer programs well known in the art such as Vector NTI Suite (InforMax, MD) software. "Variant" may also refer to a "shuffled gene," as described, for example, in U.S. Pat. Nos. 6,506,603, 6,132,970, 6,165,793 and 6,117,679.

A further way of obtaining a WAIS DNA sequence is to synthesize it ab initio from the appropriate bases, for example, by using the appropriate cDNA sequence as a template.

Nucleic Acid Constructs

The present invention includes recombinant constructs comprising one or more of the nucleic acid sequences herein. The constructs typically comprise a vector, such as a plasmid, a cosmid, a phage, a virus (e.g., a plant virus), a bacterial artificial chromosome (BAC), a yeast artificial chromosome (YAC), or the like, into which a nucleic acid sequence has been inserted, in a forward or reverse orientation. Large numbers of suitable vectors are known and commercially available and need not be reiterated here.

Recombinant nucleic acid constructs may be made using standard techniques. For example, a nucleotide sequence for transcription may be obtained by treating a vector containing said sequence with restriction enzymes to cut out the appropriate segment. The nucleotide sequence for transcription may also be generated by annealing and ligating synthetic oligonucleotides or by using synthetic oligonucleotides in a polymerase chain reaction (PCR) to give suitable restriction sites at each end. The nucleotide sequence then is cloned into a vector containing suitable regulatory elements, such as upstream promoter and downstream terminator sequences. Typically, plant transformation vectors include one or more cloned plant coding sequence (genomic or cDNA) under the transcriptional control of 5' and 3' regulatory sequences and a selectable marker. Such plant transformation vectors typically also contain a promoter, a transcription initiation start site, an RNA processing signal (such as splicing signal sequences), a transcription termination site, and/or a polyadenylation signal. Enhancers and targeting sequences may also be present.

The invention provides nucleic acid molecules likely to cause altered fiber length and plant height in a transformed plant. An important aspect of the present invention is the use of nucleic acid constructs wherein a wall-associated kinase-encoding nucleotide sequence is operably linked to one or more promoters, which drive expression of the wall-associated kinase-encoding sequence in a constitutive manner or in certain cell types, organs, or tissues so as to alter the fiber length of a transformed plant compared to the fiber length of a non-transgenic plant.

Suitable constitutive plant promoters which can be useful for expressing the wall-associated kinase sequences suitable for the present invention include but are not limited to the cauliflower mosaic virus (CaMV) 35S promoter, the maize and the *Populus* polyubiquitin promoters, which confer constitutive, high-level expression in most plant tissues (see, e.g., WO 2007/00611, U.S. Pat. No. 5,510,474; Odell et al., *Nature*, 1985, 313: 810-812); the nopaline synthase promoter (An et al., 1988, *Plant Physiol.* 88: 547-552); the FMV promoter from figwort mosaic virus (U.S. Pat. No. 5,378,619) and the octopine synthase promoter (Fromm et al., 1989, *Plant Cell* 1: 977-984).

The promoter can also be chosen so that the expression occurs at a determined time point in the plant's development, or at a time point determined by outside influences, or in a tissue-specific or tissue-preferred manner. For example, it may ensure specific or preferred expression in fibers cells (cotton fiber-, xylem fiber-, or extra xylary fiber-specific or -preferred promoters).

Exemplary cotton fiber-specific or -preferred promoters include, for example, the cotton CFACT1 gene promoter (U.S. Pat. No. 6,995,256); the E6 gene promoter (U.S. Pat. No. 6,096,950, John et al., 1996, *Plant Mol. Biol.* 30: 297-306; John et al., 1996, *Proc. Natl. Acad. Sci.* 93: 12768-12773); H6 gene promoter (John et al., 1995, *Plant Physiol.* 108: 669-676); GhTUB1 gene promoter (Li et al., 2002, *Plant Physiol.* 130: 666-674) and FbL2A (Rinehart et al., 1996, *Plant Physiol.* 112: 1331-1341 and John et al., 1996, *Proc. Natl. Acad. Sci. USA* 93: 12768-12773).

Vascular system-preferred or -specific promoters, such as xylem-preferred promoters, may be useful for effecting expression of nucleic acid molecules within the invention, specifically in vascular tissue, especially xylem tissue. Thus, "xylem-preferred" means that the nucleic acid molecules of the current invention are more active in the xylem than in any other plant tissue. The selected promoter should cause the overexpression of the wall-associated kinase, pursuant to the invention, thereby to modify the length of the cell xylem, to modify the height of the host plant, or both.

Suitable promoters are illustrated by but are not limited to the xylem-preferred tubulin (TUB) gene promoter, the caffeic acid 3-O-methyltransferase gene promoter (COMT), the sucrose synthase gene promoter (SuSy), and the xylem-preferred coumarate-4-hydroxylase (C4H) gene promoter. Other suitable xylem-preferred promoters are disclosed in international patent application WO 2005/096805, which is incorporated here by reference.

Synthetic promoters including specific nucleotide regions conferring tissue-specific or tissue-preferred expression may also be used, as exemplified by identification of regulatory elements within larger promoters conferring xylem-preferred expression. Seguin et al., 1997, *Plant Mol. Biol.* 35: 281-291; Torres-Schumann et al., 1996, *Plant J.* 9: 283-296; and Leyva et al., 1992, *Plant Cell* 4: 263-271.

Although the gene expression rate is mainly modulated by the promoter, improvement in expression may also be achieved by the identification and use of enhancer sequences, such as intronic portions of genes, which elevate the expression level of the nearby located genes in an independent manner orientation. In plants, the inclusion of some introns in gene constructs in a position between the promoter and the gene coding sequence leads to increases in mRNA and protein accumulation. Introns known to elevate expression in plants have been identified in maize genes, for example, hsp70, tubA1, Adh1, Sh1, UbH (Brown and Santino, U.S. Pat. Nos. 5,424,412 and 5,859,347; Jeon et al., 2000, *Plant Physiol.* 123: 1005-1014; Callis et al., 1987, *Genes Dev.* 1: 1183-1200; Vasil et al., 1989, *Plant Physiol.* 91: 1575-1579), and in dicotyledonous plant genes such as rbcS from petunia (Dean et al., 1989, *Plant Cell* 1: 201-208); ST-LS1 from potato (Leon et al., 1991, *Plant Physiol.* 95: 968-972) and UBQ3 (Norris et al., 1993, *Plant Mol. Biol.* 21: 895-906) and PAT1 from *Arabidopsis thaliana* (Rose and Last, 1997, *Plant J.* 11: 455-464).

In accordance with one aspect of the invention, a wall-associated kinase sequence is incorporated into a nucleic acid construct that is suitable for plant transformation. Accordingly, nucleic acid constructs are provided comprising a wall-associated kinase sequence, under the control of a transcriptional initiation region operative in a plant, so that the construct can generate RNA in a host plant cell. Preferably, the transcriptional initiation region is part of a vascular or xylem-preferred promoter, such as any of those mentioned above. Such a nucleic acid construct can be used to modify wall-associated kinase gene expression in plants, as described above.

Expression vectors may also contain a selection marker by which transformed cells can be identified in culture. The marker may be associated with the heterologous nucleic acid molecule, i.e., the gene operably linked to a promoter. As used herein, the term "marker" refers to a gene encoding a trait or a phenotype that permits the selection of, or the screening for, a plant or cell containing the marker. In plants, for example, the marker gene will encode antibiotic or herbicide resistance. This allows for selection of transformed cells from among cells that are not transformed or transfected.

Examples of suitable selectable markers include adenosine deaminase, dihydrofolate reductase, hygromycin-B-phosphotransferase, thymidine kinase, xanthine-guanine phospho-ribosyltransferase, glyphosate and glufosinate resistance, and amino-glycoside 3'-O-phosphotransferase (kanamycin, neomycin and G418 resistance). These markers may include resistance to G418, hygromycin, bleomycin, kanamycin, and gentamicin. The construct also may contain the selectable marker gene Bar, which confers resistance to herbicidal phosphinothricin analogs like ammonium glufosinate. Thompson et al., *EMBO J.* 6: 2519-23 (1987). Other suitable selection markers are known as well.

Visible markers such as green florescent protein (GFP) may be used. Methods for identifying or selecting transformed plants based on the control of cell division have also been described. See John and Van Mellaert, WO 2000/052168, and Fabijansk et al., WO 2001/059086.

Replication sequences, of bacterial or viral origin, may also be included to allow the vector to be cloned in a bacterial or phage host. Preferably, a broad host range prokaryotic origin of replication is used. A selectable marker for bacteria may be included to allow selection of bacterial cells bearing the desired construct. Suitable prokaryotic selectable markers also include resistance to antibiotics such as kanamycin or tetracycline.

Other DNA sequences encoding additional functions may also be present in the vector, as is known in the art. For instance, when *Agrobacterium* is the host, T-DNA sequences may be included to facilitate the subsequent transfer to and incorporation into plant chromosomes.

Plants for Genetic Engineering

The present invention comprehends the genetic manipulation of plants, especially hardwood trees, to overexpress a wall-associated kinase in vascular tissues via introducing a wall-associated gene, preferably under the control of a xylem-preferred or xylem-specific promoter. The result is enhanced fiber length and plant height.

In this description, the term "plant" denotes any fiber-containing plant material that can be genetically manipulated, including but not limited to differentiated or undifferentiated plant cells, protoplasts, whole plants, plant tissues, or plant organs, or any component of a plant such as a leaf, stem, root, bud, tuber, fruit, rhizome, or the like.

Plants that can be engineered in accordance with the invention include but are not limited to trees, such as *Eucalyptus* species (*E. alba, E. albens, E. amygdalina, E. aromaphloia, E. baileyana, E. balladoniensis, E. bicostata, E. botryoides, E. brachyandra, E. brassiana, E. brevistylis, E. brockwayi, E. camaldulensis, E. ceracea, E. cloeziana, E. coccifera, E. cordata, E. cornuta, E. corticosa, E. crebra, E. croajingolensis, E. curtisii, E. dalrympleana, E. deglupta, E. delegatensis, E. delicata, E. diversicolor, E. diversifolia, E. dives, E. dolichocarpa, E. dundasii, E. dunnii, E. elata, E. erythrocorys, E. erythrophloia, E. eudesmoides, E. falcata, E. gamophylla, E. glaucina, E. globulus, E. globulus* subsp. *bicostata, E. globulus* subsp. *globulus, E. gongylocarpa, E. grandis, E. grandis× urophylla, E. guilfoylei, E. gunnii, E. hallii, E. houseana, E. jacksonii, E. lansdowneana, E. latisinensis, E. leucophloia, E. leucoxylon, E. lockyeri, E. lucasii, E. maidenii, E. marginata, E. megacarpa, E. melliodora, E. michaeliana, E. microcorys, E. microtheca, E. muelleriana, E. nitens, E. nitida, E. obliqua, E. obtusiflora, E. occidentalis, E. optima, E. ovata, E. pachyphylla, E. pauciflora, E. pellita, E. perriniana, E. petiolaris, E. pilularis, E. piperita, E. platyphylla, E. polyanthemos, E. populnea, E. preissiana, E. pseudo globulus, E. pulchella, E. radiata, E. radiata* subsp. *radiata, E. regnans, E. risdonii, E. robertsonii, E. rodwayi, E. rubida, E. rubiginosa, E. saligna, E. salmonophloia, E. scoparia, E. sieberi, E. spathulata, E. staeri, E. stoatei, E. tenuipes, E. tenuiramis, E. tereticornis, E. tetragona, E. tetrodonta, E. tindaliae, E. torquata, E. umbra, E. urophylla, E. vernicosa, E. viminalis,*

*E. wandoo, E. wetarensis, E. willisii, E. willisii* subsp. *falciformis, E. willisii* subsp. *willisii, E. woodwardii*), *Populus* species (*P. alba, P. alba×P. grandidentata, P. alba×P. tremula, P. alba×P. tremula* var. *glandulosa, P. alba×P. tremuloides, P. balsamifera, P. balsamifera* subsp. *trichocarpa, P. balsamifera* subsp. *trichocarpa×P. deltoides, P. ciliata, P. deltoides, P. euphratica, P. euramericana, P. kitakamiensis, P. lasiocarpa, P. laurifolia, P. maximowiczii, P. maximowiczii×P. balsamifera* subsp. *trichocarpa, P. nigra, P. sieboldii×P. grandidentata, P. suaveolens, P. szechuanica, P. tomentosa, P. tremula, P. tremula×P. tremuloides, P. tremuloides, P. wilsonii, P. canadensis, P. yunnanensis*), Conifers such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

Fiber-producing plants also are included in this context. Illustrative crops are cotton (*Gossipium* spp.), flax (*Linum usitatissimum*), stinging nettle (*Urtica dioica*), hop (*Humulus lupulus*), lime trees (*Tilia cordata, T.×. europaea* and *T. platyphyllus*), spanish broom (*Spartium junceum*), ramie (*Boehmeria nivea*), paper mulberry (*Broussonetya papyrifera*), New Zealand flax (*Phormium tenax*), dogbane (*Apocynum cannabinum*), *Iris* species (*I. douglasiana, I. macrosiphon* and *I. purdyi*), milkweeds (*Asclepia* species), pineapple, banana and others. Also contemplated are forage crops, such as alfalfa, lolium, festuca and clover.

In the present description, "transgenic plant" refers to a plant that has incorporated a nucleic acid sequence, including but not limited to genes that are not normally present in a host plant genome, nucleic acid sequences not normally transcribed into RNA or translated into a protein, or any other genes or nucleic acid sequences that one desires to introduce into the wild-type plant, such as genes that normally may be present in the wild-type plant but that one desires either to genetically engineer or to have altered expression. The "transgenic plant" category includes both a primary transformant and a plant that includes a transformant in its lineage, e.g., by way of standard introgression or another breeding procedure.

A "hybrid plant" refers to a plant or a part thereof resulting from a cross between two parent plants, wherein one parent is a genetically engineered plant of the invention. Such cross can occur naturally by, for example, sexual reproduction, or artificially by, for example, in vitro nuclear fusion. Methods of plant breeding are well-known and within the level of one of ordinary skill in the art of plant biology.

In contrast, a plant that is not genetically manipulated is a control plant and is referred to as a "non-transgenic" or "control" plant. Non-transgenic plant can be a plant which genome is neither modified by the introduction of a construct comprising the polynucleotide sequences or fragment thereof of the present invention. It can also be a plant regenerated from cultured cells or tissues without prior modification by the introduction of a construct comprising the polynucleotide sequence of the invention, or may comprise a homozygote recessive progeny (i.e., do not have any copy of the transgene) resulting from self-fertilization of a transgenic plant.

It is contemplated that, in some instances, the genome of an inventive transgenic plant will have been augmented through the stable introduction of a transgene. In other instances, however, the introduced gene will replace an endogenous sequence. A preferred gene in the regard, pursuant to the present invention, is a wall-associated kinase DNA sequence, for example, one obtained from *Arabidopsis thaliana*.

Methods for Genetic Engineering

Constructs according to the invention may be introduced into any plant cell, using a suitable technique. Both monocotyledonous and dicotyledonous angiosperm or gymnosperm plant cells may be genetically engineered in various ways known to the art. For example, see Klein et al., 1993, *Biotechnology* 4: 583-590; Bechtold et al., 1993, *C. R. Acad. Sci. Paris* 316: 1194-1199; Koncz and Schell, 1986, *Mol. Gen. Genet.* 204: 383-396; Paszkowski et al., 1984, *EMBO J.* 3: 2717-2722; Sagi et al., 1994, *Plant Cell Rep.* 13: 262-266.

*Agrobacterium* species such as *A. tumefaciens* and *A. rhizogenes* can be used, for example, in accordance with Nagel et al., 1990, *Microbiol Lett* 67: 325. In brief, *Agrobacterium* may be used with a plant expression vector via, e.g., electroporation, after which the *Agrobacterium* is introduced to plant cells via, e.g., the well known leaf-disk method.

Additional methods for accomplishing this include, but are not limited to, transformation by *Rhizobium, Sinorhizobium* or *Mesorhizobium* (Broothaerts et al., 2005, *Nature* 433: 629-633), electroporation, particle gun bombardment, calcium phosphate precipitation, and polyethylene glycol fusion, transfer into germinating pollen grains, direct transformation (Lorz et al., 1985, *Mol. Genet.* 199: 179-182), and other methods known to the art. If a selection marker, such as kanamycin resistance, is employed, it makes it easier to determine which cells have been successfully transformed.

The *Agrobacterium* transformation methods discussed above are known to be useful for transforming dicots. Additionally, de la Pena et al., 1987, *Nature* 325: 274-276; Rhodes et al., 1988, *Science* 240: 204-207; and Shimamoto et al., 1989, *Nature* 328: 274-276, all of which are incorporated by reference, have transformed cereal monocots using *Agrobacterium*. Also see Bechtold and Pelletier, 1998, *Methods Mol. Biol.* 82: 259-266, showing the use of vacuum infiltration for *Agrobacterium*-mediated transformation.

The presence of a protein, polypeptide, or nucleic acid molecule in a particular cell can be measured to determine if, for example, a cell has been successfully transformed or transfected. The ability to carry out such assay is well known and need not be reiterated here.

Quantifying Fiber Length and Plant Height

The word "fiber" is often used to unify a diverse group of plant cell types that share in common the features of having an elongated shape and abundant cellulose in thick cell walls, usually, but not always, described as secondary walls. Such walls may or may not be lignified, and the protoplast of such cells may or may not remain alive at maturity. In some industries, the term "fiber" is usually inclusive of thick-walled conducting cells such as vessels and tracheids and to fibrillar aggregates of many individual fiber cells. For the purposes of the present invention, the term "fiber" includes: (a) conducting and non-conducting cells of the xylem; (b) fibers of extraxylary origin, including those from phloem, bark, ground tissue, and epidermis; and (c) fibers from stems, leaves, roots, seeds, and flowers or inflorescences.

Transgenic plants of the invention are characterized by increased fiber length and preferably increased height as well. Increased fiber length in the genetically engineered plant is preferably achieved via WAK overexpression in the plant tissues wherein cell expansion occurs. In describing a plant of the invention, "increased fiber length" refers to a quantitative augmentation in the length of fiber cells in the plant when compared to the length of fiber cells in a wild-type plant". A quantitative increase of fiber length can be measured by several techniques, such as digitizing, the Kajaani procedure, and the Fiber Quality Analyzer. Han et al., 1999, In: Kenaf Properties, Processing and Products, Mississippi State University, Ag & Bio Engineering, pp 149-167.

The fiber length in the engineered plant of the invention is at least from 5 to 15% longer, preferably at least 10-30% and most preferably at least from 20-50% longer than the fiber length of the wild-type plant.

Because increased fiber length can be followed by an increase in plant height, transgenic plants of the invention may have increase fiber length and height. In this description, therefore, the phrase "increased plant height" connote a quantitative increase in plant height, when compared to the height of a wild-type plant. The height in the engineered plant of the invention can be increased to levels of about 5% to about 90%, preferably about 10% to about 75%, even more preferably about 15% to about 65% of the height of the wild-type plant.

\* \* \*

Specific examples are presented below of methods for obtaining wall-associated kinase genes, as well as for introducing the target gene, via *Agrobacterium*, to produce plant transformants. They are meant to be exemplary and not as limitations on the present invention.

EXAMPLE 1

Isolation of a Wall-Associated Kinase DNA Sequence from *Arabidopsis thaliana*

(a) RNA Preparation from *Arabidopsis thaliana* Stem and cDNA Synthesis

Stem cuttings of three-months-old *Arabidopsis thaliana* plants were cut in small pieces, frozen in liquid nitrogen, and used for RNA extraction via the cetyltrimethyl-ammonium bromide (CTAB) extraction method. Aldrich and Cullis, 1993, *Plant Mol. Biol. Report,* 11: 128-141. A cDNA pool was used in RT-PCR experiments in which the isolated total RNA was used as template, and Superscript II reverse transcriptase (Invitrogen) and oligo(dT) primer were used to synthesize the first-strand cDNA. Double-stranded cDNA was obtained by the subsequent polymerase reaction, using gene-specific primers, as described below.

(b) Primer Design

A cDNA sequence representing the wall-associated kinase 4 mRNA from *Arabidopsis thaliana* has been determined and deposited in the GenBank under accession number NM101974. Based on this sequence, DNA oligomers were synthesized as primers for PCR, including either the region around the first codon ATG or around the termination codon of the main ORF encoding the wall-associated kinase 4.

Primers were designed to amplify the entire coding region of the wall-associated kinase 4 ORF, i.e., from the ATG through the translation stop codon. The sequences of the primers are given below:

```
WAK_NDE  Length: 23        SEQ ID NO: 11
CATATGAAAGTGCAGCGTCTGTT

WAK_XBA  Length: 23        SEQ ID NO: 12
TCTAGATCAGCGGCCTGCTTCAA
```

(c) PCR Amplification

The cDNA sample obtained in (a) was used as template, and the primers designed in (b) were used for PCR. The PCR steps involved 40 cycles of 1 minute at 94° C., 1 minute at 50° C., and 2 minutes at 72° C. followed by an extra step of elongation at 72° C. for 7 minutes. The PCR products were isolated by gel electrophoresis on 1.0% agarose followed by ethidium bromide staining of the electrophoresed gel and detection of amplified bands on a UV transilluminator. The detected amplified band was verified and cut out of the agarose gel with a razor. The pieces of gel were transferred to 1.5 mL microtubes, and the DNA fragments were isolated and purified using a GFX PCR clean-up and gel band purification kit (Amersham). The recovered DNA fragments were subcloned to the pGEM-T cloning vector (Promega), transformed into *E. coli*, and then used to prepare plasmid DNA in the usual manner, which was then sequenced by the dideoxy method (Messing, 1983, *Methods in Enzymol.* 101: 20-78), using BigDye chemistry (Applied Biosystems), to yield the DNA sequence disclosed here as SEQ ID NO: 1, for use pursuant to the present invention.

EXAMPLE 2

Preparation of Transgenic *Nicotiana tabacum* Plants

The wall-associated kinase gene obtained in Example 1 above was introduced into a plant host to produce transgenic *Nicotiana tabacum* plants.

(a) Preparation of Constructs and Transformation of *Agrobacterium*

Expression constructs were prepared by cleaving the wall-associated kinase gene obtained in Example 1 above with suitable restriction enzymes so as to include all of the open reading frame and inserting the gene into the plant transformation vector pALELLYX-WAK (FIG. 1) together with an appropriate promoter. For example, the wall-associated kinase gene obtained in Example 1 was cloned into the aforementioned expression vector downstream to a xylem-preferred tubulin gene (TUB) promoter from *Populus deltoides*, as set forth in international application WO 2005/096805. The resulting expression construct was amplified in *E. coli*, and then transformed by freeze thawing into *Agrobacterium tumefaciens* LBA4404 strain.

(b) *Agrobacterium*-Mediated Transformation of *Nicotiana tabacum*

Transformation of *Nicotiana* sp. was accomplished using the leaf disk method of Horsch et al., 1985, *Science* 227: 1229, using a nucleic acid construct comprising the wall-associated kinase gene obtained in (a) operably linked to the TUB promoter of a xylem-preferred gene. The transformants were selected on Murashige and Skoog medium (Sigma, St. Louis, Mo.) containing 100 milligrams/liter of kanamycin and 500 mg/L carbenicillin (Sigma). The transformed tobacco shoots were allowed to root on the Murashige and Skoog medium, and were subsequently transferred to soil and grown in the greenhouse.

(c) PCR Verification of Foreign Gene Insertion into the Host Plant Genome

PCR can be used to verify the integration of the gene construct in the genome of transgenic plants. The PCR reaction mixture contained 100 ng genomic DNA of transformed plant, and 0.2 µM of each primer described above, 100 µM of each deoxyribonucleotide triphosphate, 5 µL PCR buffer and 2.5 Units of AmpliTaq DNA polymerase (Applied Biosystems) in a total volume of 50 µL. The cycling parameters were as follows: 94° C. for 1 minute, 50° C. for 1 minute and 72° C. for 3 minutes, for 40 cycles, with 5 minutes at 72° C. extension. The PCR products were electrophoresized on a 1% agarose gel.

(d) Determination of Transgene Expression Level in Transgenic Plants

Semi-quantitative RT-PCR was used to detect the accumulation of wall-associated kinase transcripts in stem tissue of the transgenic plants. Total RNA was isolated from stem cuts of 3-months old transgenic *Nicotiana* T0 and T1 plants using the CTAB method described by Aldrich and Cullis, 1993, *Plant Mol. Biol. Report.* 11: 128-141.

cDNA was synthesized from 500 ng of total RNA using Superscript II RNase H-RT (Invitrogen, USA). The primers described above were used along with primers for the constitutive gene encoding glyceraldehyde-3-phosphate dehydrogenase (GAPDH) as an internal control to normalize the quantity of total RNA used in each sample. PCR was done with a 12.5-fold dilution of the first-strand cDNA under the following conditions: 94° C. for 3 minutes and 27 cycles of 94° C. for 1 minute, 52 to 60° C. for 45 seconds, and 72° C. for 1 minute and 30 seconds.

EXAMPLE 3

Increase in Fiber Length in Tobacco Transgenic Plants Overexpressing Wall-Associated Kinase Gene in Vascular Tissues Stem regions corresponding to 50% height of transgenic and control plants of 5 months old were macerated in acetic acid-peroxide solution at 70° C. for 48 hours or until single cells were obtained. Cells were stained with safranine and examined under a microscope (Leica DMIL) fitted with a camera (Sony) linked to a personal computer. Cells (about 100 per line) were measured directly on the screen, using the "Image Tool" software.

Figure 2:
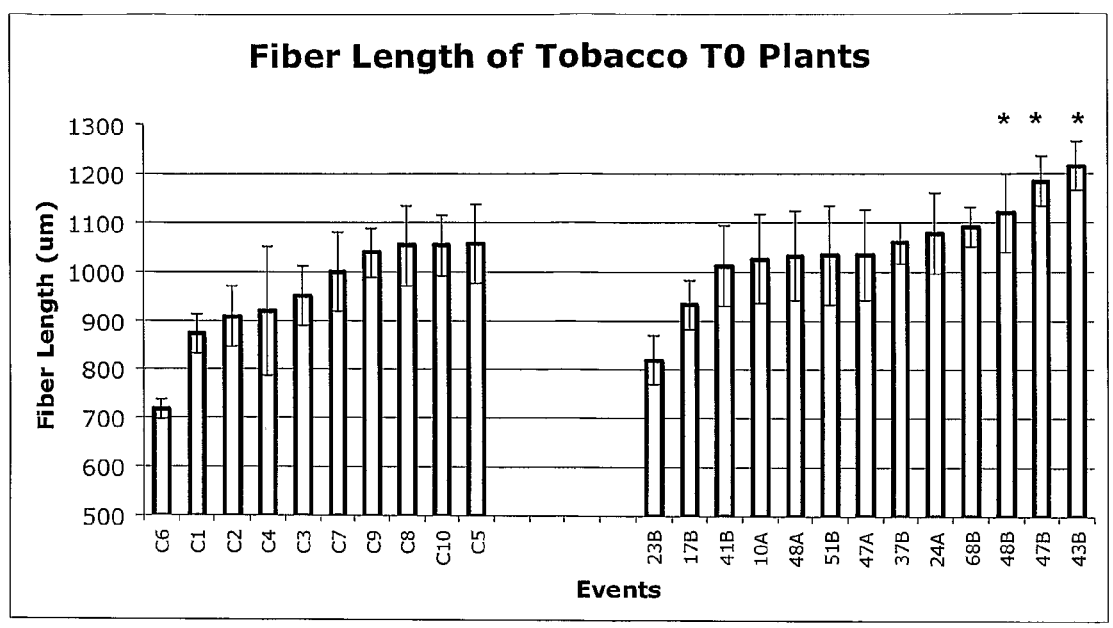
FIG. 2 shows the fiber length of several transgenic lines transformed with the plant expression plasmidial vector pALELLYX-WAK of the invention and respective control non-transgenic plants. Asterisk denotes statistically significant higher mean fiber length values ($P<0.05$, t-test).

Three of the transgenic events, known to express the transgene according to procedure detailed in Example 2, showed a statistically significant increase in fiber length (FIG. 2). Transgenic event 43B exhibits an increase of 21% in fiber length as compared to the control plants ($P<0.05$, t-test). Transgenic event 47B exhibits an increase of 19% in fiber length when compared to the control plants (FIG. 2; $P<0.05$, t-test). Additionally, transgenic event 43B exhibit an increase of 15% in fiber length as compared to the control plants (FIG. 2 $P<0.05$, t-test).

It is important to mention that another strategy to increase fiber length by the overexpression of a pectin methyl esterase gene (Berthold et al., WO 2006/068603) has achieved an increase of only 5% on fiber length of transgenic plants when compared to control plants.

Figure 3:
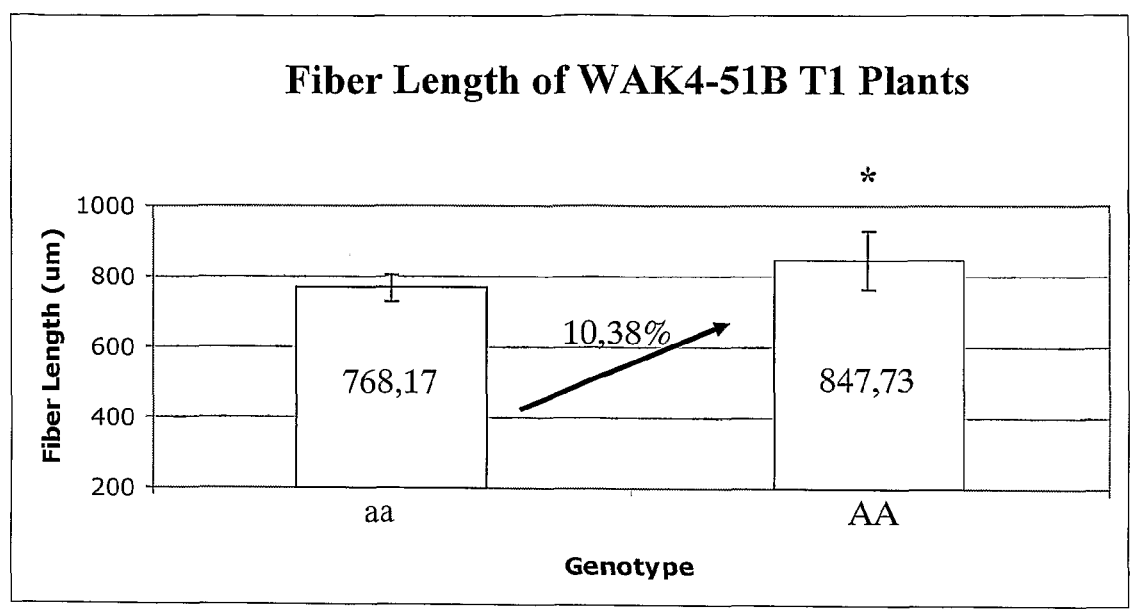
FIG. 3 shows the fiber length of two genotypes of a T1 transgenic plant (line 51B) transformed with the plant expression plasmidial vector pALELLYX-WAK of the invention. Asterisk denotes statistically significant higher mean fiber length values ($P<0.05$, t-test).
Figure 4:
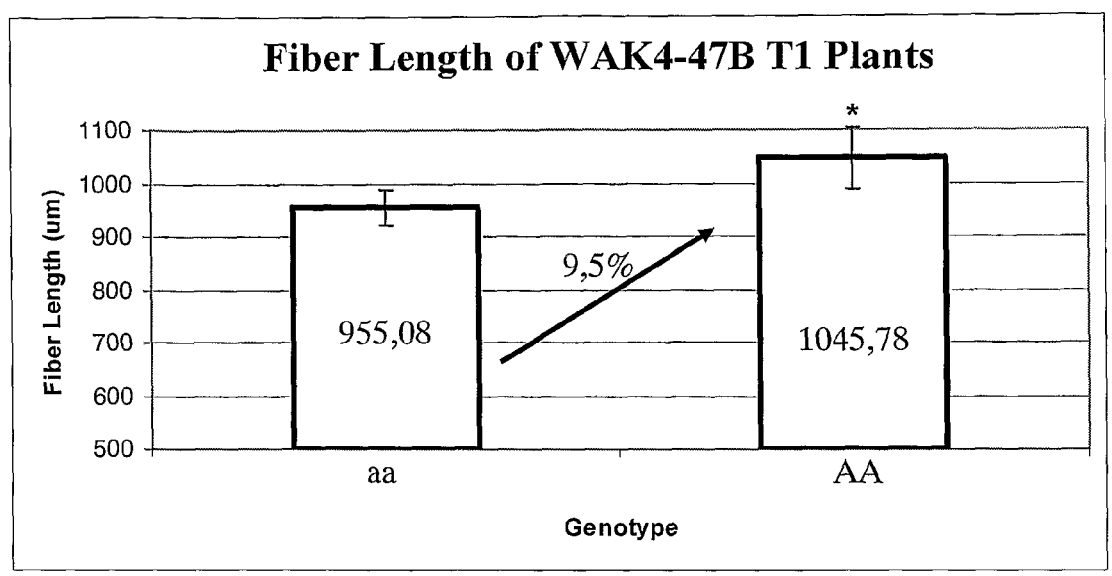
FIG. 4 shows the fiber length of two genotypes of a T1 transgenic plant (line 47B) transformed with the plant expression plasmidial vector pALELLYX-WAK of the invention. Asterisk denotes statistically significant higher mean fiber length values ($P<0.05$, t-test).

After grown to maturity, the T0 events were selfed to generate T1 lines. Plants that are homozygote dominant present a significant increase of 10% in fiber length ($P<0.05$, t-test), when compared to homozygote recessive plants. These results were observed in two different lines (FIG. 3 and FIG. 4).

EXAMPLE 4

Increase in Plant Height in Tobacco Transgenic Plants Overexpressing Wall-Associated Kinase Gene in Vascular Tissues $T_1$ progeny resulting from self-fertilization of transgenic plants was individually potted 3 weeks after sowing. Growth was measured periodically until the first flower was formed (plants were about 5 months old), and was recorded as total height.

Figure 5:
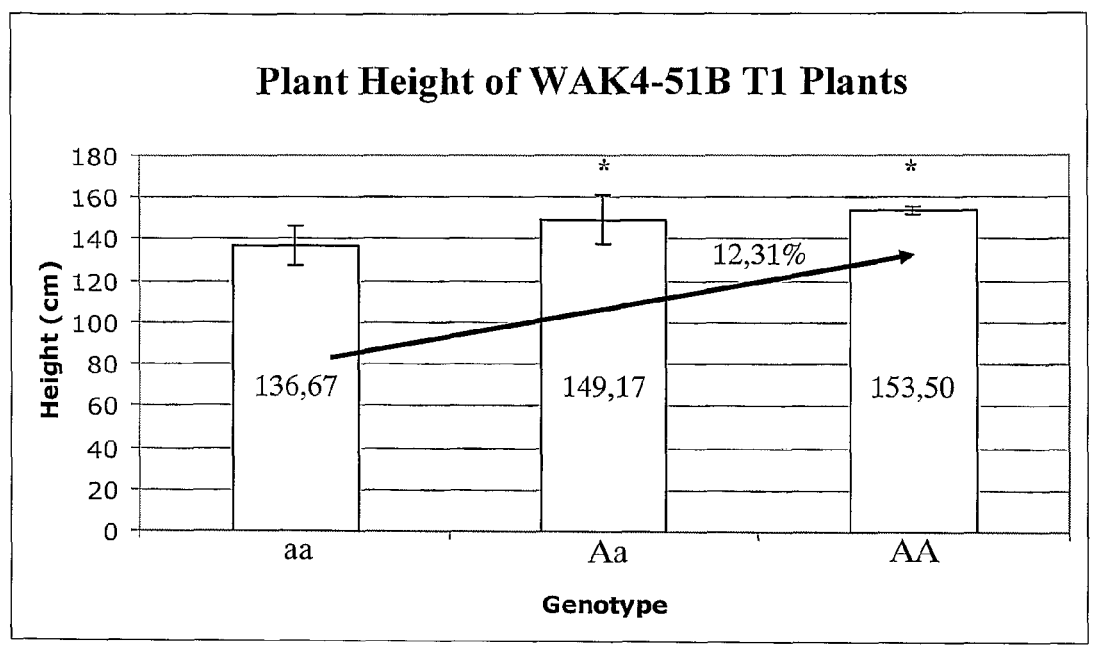
FIG. 5 shows the plant height of the three genotypes of a T1 transgenic line (line 51B) transformed with the plant expression plasmidial vector pALELLYX-WAK of the invention. Asterisk denotes statistically significant higher mean plant height values ($P<0.05$, t-test).

The results presented are an example of the increase in plant height observed in the homozygote dominant plants of different lines. Plant height of the three genotypes from the event 51B was compared. Plants that are homozygote dominant are 12% higher than the homozygote recessive plants. Plants that are hemizygote are 9% higher than the homozygote recessive plants ($P<0.05$, t-test) (FIG. 5).

EXAMPLE 5

Preparation of Transgenic *Populus* Plants

The gene obtained in Example 1 above was introduced into a plant host to produce transgenic *Populus* plants.

(a) Preparation of Constructs and Transformation of *Agrobacterium*

Expression constructs can be prepared by cleaving the wall-associated kinase gene obtained in Example 1 above with suitable restriction enzymes so as to include the entire open reading frame and inserting the gene into the plant transformation vector pALELLYX-WAK (FIG. 1) together with an appropriate promoter. For example, the wall-associated kinase gene obtained in Example 1 was cloned into the aforementioned expression vector downstream to a xylem-preferred tubulin gene (TUB) promoter from *Populus deltoides*, as set forth in international application WO 2005/096805. The resulting expression construct was amplified in *E. coli*, and then transformed by freeze thawing into *Agrobacterium tumefaciens* LBA4404 strain.

(b) *Agrobacterium*-Mediated Transformation of *Populus*

Wild-type aspen was transformed with *Agrobacterium tumefaciens* carrying a construct comprising an *Arabidopsis thaliana* wall-associated kinase gene obtained in Example 1 operably linked to the promoter of a xylem-preferred gene (TUB). Petioles and internodal stem segments from in vitro micropropagated plants were used as explants. Transformed shoots are selected on regeneration medium containing 100 mg/L of kanamycin and allowed to root on the Murashige and Skoog medium. Selected plants are subsequently transferred to soil and grown in the greenhouse.

What is claimed is:

1. A nucleic acid construct for increasing fiber length and/or plant height. said construct comprising a wall-associated kinase 4 (WAK4) polynucleotide sequence operably linked to a xylem-preferred promoter that causes overexpression of said WAK4 polynucleotide sequence, wherein said WAK4 polynucleotide sequence encodes a polypeptide having at least 95% or more amino acid sequence identity to SEQ ID NO: 2.

2. The nucleic acid construct of claim 1, wherein said xylem-preferred promoter is selected from the group consisting of TUB gene promoter, SuSy gene promoter, COMT gene promoter and C4H gene promoter.

3. A transgenic plant comprising a nucleic acid construct comprising a WAK4 polynucleotide sequence operably linked to a xylem-preferred promoter that causes overexpression of said WAK4 polynucleotide sequence, wherein said WAK4 polynucleotide sequence encodes a polypeptide having at least 95% or more amino acid sequence identity to SEQ ID NO: 2, wherein said plant has an increase in fiber length and/or plant height compared to a non-transgenic plant of the same species.

4. The transgenic plant of claim 3, wherein the xylem-preferred promoter is selected from the group consisting of TUB gene promoter, SuSy gene promoter, COMT gene promoter, and C4H gene promoter.

5. The transgenic plant of claim 3, wherein said plant is a dicotyledon plant.

6. The transgenic plant of claim 3, wherein said plant is a monocotyledon plant.

7. The transgenic plant of claim 3, wherein said plant is a gymnosperm.

8. The transgenic plant of claim 3, wherein said plant is a hardwood tree.

9. The transgenic plant of claim 8, wherein said hardwood tree is an *Eucalyptus* tree.

10. The transgenic plant of claim 8, wherein said hardwood tree is a *Populus* tree.

11. The transgenic plant of claim 7, wherein said gymnosperm is a *Pinus* tree.

12. A part of the transgenic plant of claim 3, wherein said part is selected from the group consisting of a leaf, a stem, a flower, an ovary, a fruit, a seed, and a callus, and wherein said part comprises said nucleic acid construct.

13. A progeny of the transgenic plant of claim 3, wherein said progeny comprises said nucleic acid construct.

14. The progeny of claim 13, wherein said progeny is a hybrid plant and wherein said hybrid plant comprises said nucleic acid construct.

15. A method for increasing fiber length and/or plant height, comprising:
  (a) introducing into a plant cell a nucleic acid construct comprising a WAK4 polynucleotide sequence operably linked to a xylem-preferred promoter that causes overexpression of said WAK4 polynucleotide sequence, wherein said WAK4 polynucleotide sequence encodes a polypeptide having at least 95% or more amino acid sequence identity to SEQ ID NO: 2;
  (b) culturing said plant cell under conditions that promote growth of a plant; and
  (c) selecting a transgenic plant that has increased fiber length and/or plant height compared to a non-transgenic plant of the same species.

16. The method of claim 15, wherein said xylem-preferred promoter is selected from the group consisting of TUB gene promoter, SuSy gene promoter, COMT gene promoter, and C4H gene promoter.

17. A wood pulp composition comprising a WAK4 polynucleotide sequence operably linked to a xylem-preferred promoter that causes overexpression of said WAK4 polynucleotide sequence, wherein said WAK4 polynucleotide sequence encodes a polypeptide having at least 95% or more amino acid sequence identity to SEQ ID NO: 2.

18. A wood fiber composition comprising a WAK4 polynucleotide sequence operably linked to a xylem-preferred promoter that causes overexpression of said WAK4 polynucleotide sequence, wherein said WAK4 polynucleotide sequence encodes a polypeptide having at least 95% or more amino acid sequence identity to SEQ ID NO: 2.

19. The transgenic plant of claim 3, wherein said WAK4 polynucleotide sequence encodes the polypeptide of SEQ ID NO:2.

* * * * *